(12) United States Patent
Frank et al.

(10) Patent No.: US 6,518,067 B1
(45) Date of Patent: Feb. 11, 2003

(54) AUTOMATED CHEMICAL SYNTHESIS APPARATUS

(75) Inventors: Ronald Frank, Braunschweig (DE); Stefan Matysiak, Braunschweig (DE); Olaf Schreuer, Braunschweig (DE); Heinrich Gausepohl, Langenfeld (DE); Andre Rosenthal, Jena (DE)

(73) Assignees: Gesellschaft fuer Biotechnologische Forschung mbH (GBF), Braunschweig (DE); Abimed Analysen-Technik GmbH, Langenfeld (DE); IMB Institut fuer Molekulare Bio technologie e.v., Jena (DE)

( * ) Notice: Subject to any disclaimer, the term of this patent is extended or adjusted under 35 U.S.C. 154(b) by 0 days.

(21) Appl. No.: 09/367,120

(22) PCT Filed: Feb. 17, 1998

(86) PCT No.: PCT/EP98/00901
§ 371 (c)(1),
(2), (4) Date: Nov. 30, 1999

(87) PCT Pub. No.: WO98/35753
PCT Pub. Date: Aug. 20, 1998

(30) Foreign Application Priority Data

Feb. 17, 1997 (DE) .......................... 197 06 089

(51) Int. Cl.[7] .................. C07H 21/02; C07H 27/12; B32B 27/04; B01J 10/00; B01J 8/00
(52) U.S. Cl. ............... 436/23.1; 422/131; 422/187; 422/236; 422/238; 422/239; 435/7.1
(58) Field of Search .................. 422/111, 131, 422/187, 236, 238, 239, 237; 435/7.1; 436/23.1

(56) References Cited

U.S. PATENT DOCUMENTS

| 5,368,823 A | * 11/1994 | McGraw et al. ............ 422/134 |
| 5,472,672 A | * 12/1995 | Brennan ..................... 422/131 |
| 5,609,826 A | * 3/1997 | Cargill et al. ................ 422/99 |

* cited by examiner

Primary Examiner—Joseph K. McKane
Assistant Examiner—Tomas Friend
(74) Attorney, Agent, or Firm—Frommer Lawrence & Haug LLP; Ronald R. Santucci

(57) ABSTRACT

The disclosed synthesis system is based on the idea of designing a synthesis and treatment procedure, substrates and anchor groups which enable biomolecules to be simultaneously produced in an entirely automatic manner. By using a pipetting robot to dispense the reagents, the reaction column can be arranged in a format suitable for subsequent treatment. For a pipetting robot to carry out even water-sensitive or air-sensitive synthesis protocols, certain structural measures must be taken. The operation principle of the automated and the synthesis sequence are described below as an example of a possible solution. The automation can work with conventional substrates and reagents. Handling, however, is simplified by new, specially adapted substrates and anchor groups. A special, simultaneous purification and aliquot portioning process improves product quality and makes the device easier to use.

18 Claims, 8 Drawing Sheets

FIG. 7
Reactors
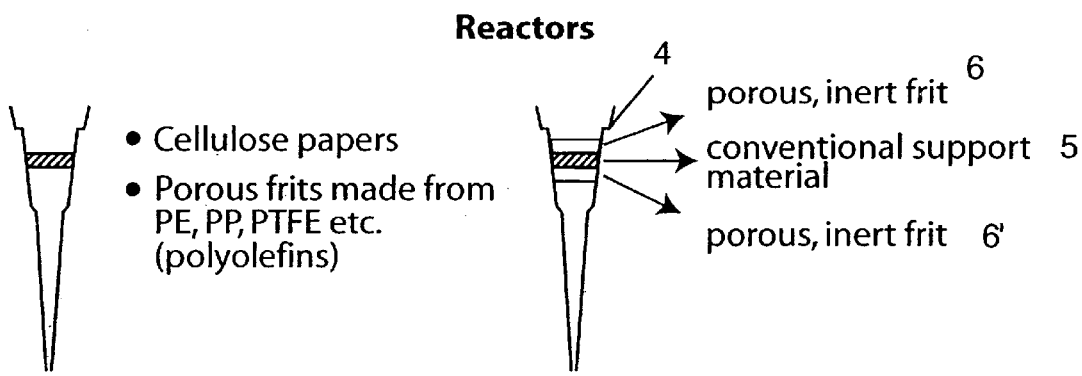
- Cellulose papers
- Porous frits made from PE, PP, PTFE etc. (polyolefins)
4
6 porous, inert frit
5 conventional support material
6' porous, inert frit
Reactor arrangement
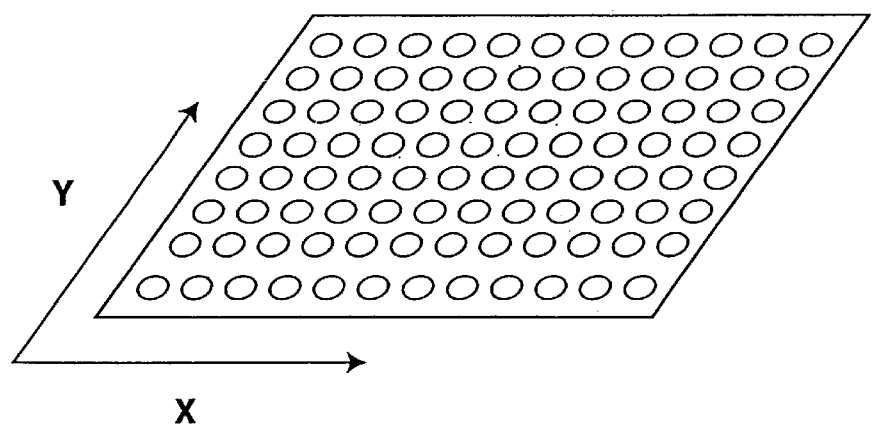
FIG. 1A
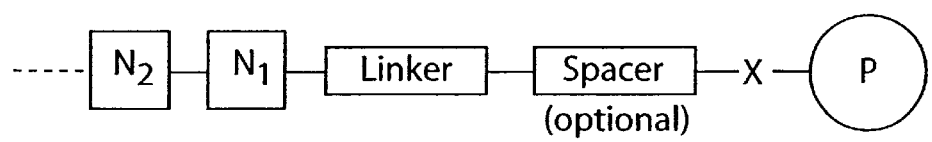

Key
 monomer bases A, G, T, C
 tetrazole
 base-protecting group
 saftey-catch linker
 phosphite-protecting group (=β-cyanoethyl)
DMTr    DMTr - protecting group
 diisopropylamine group
 capping group

FIG. 2
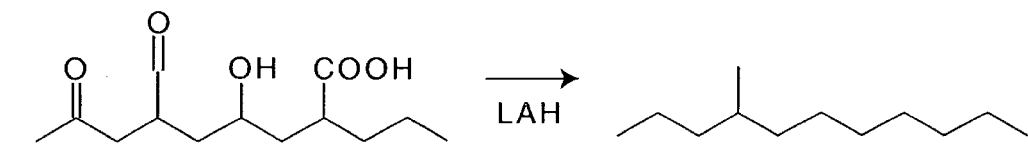
PE from various manufacturers
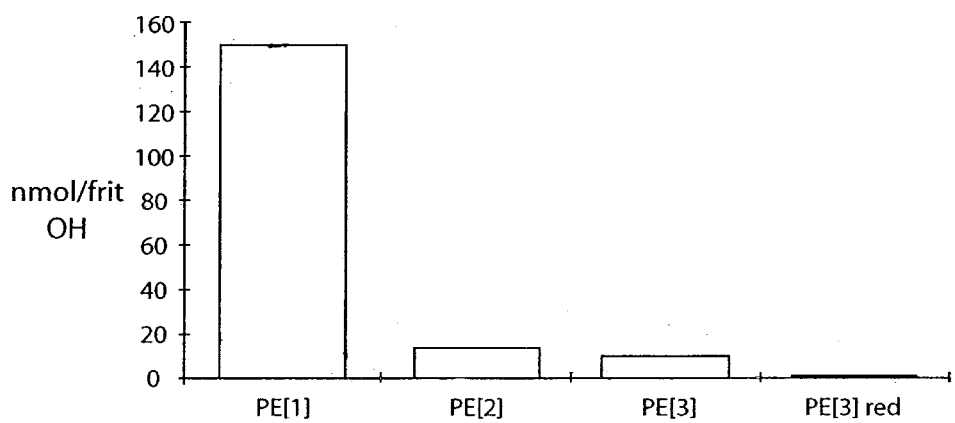
FIG. 3
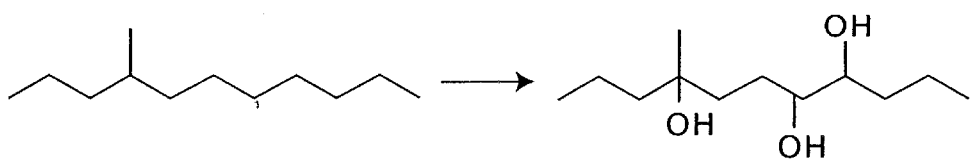
PE hydroxylation
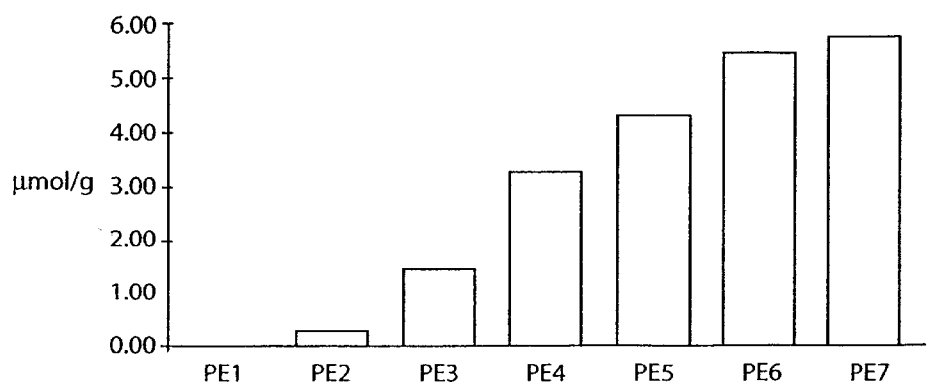

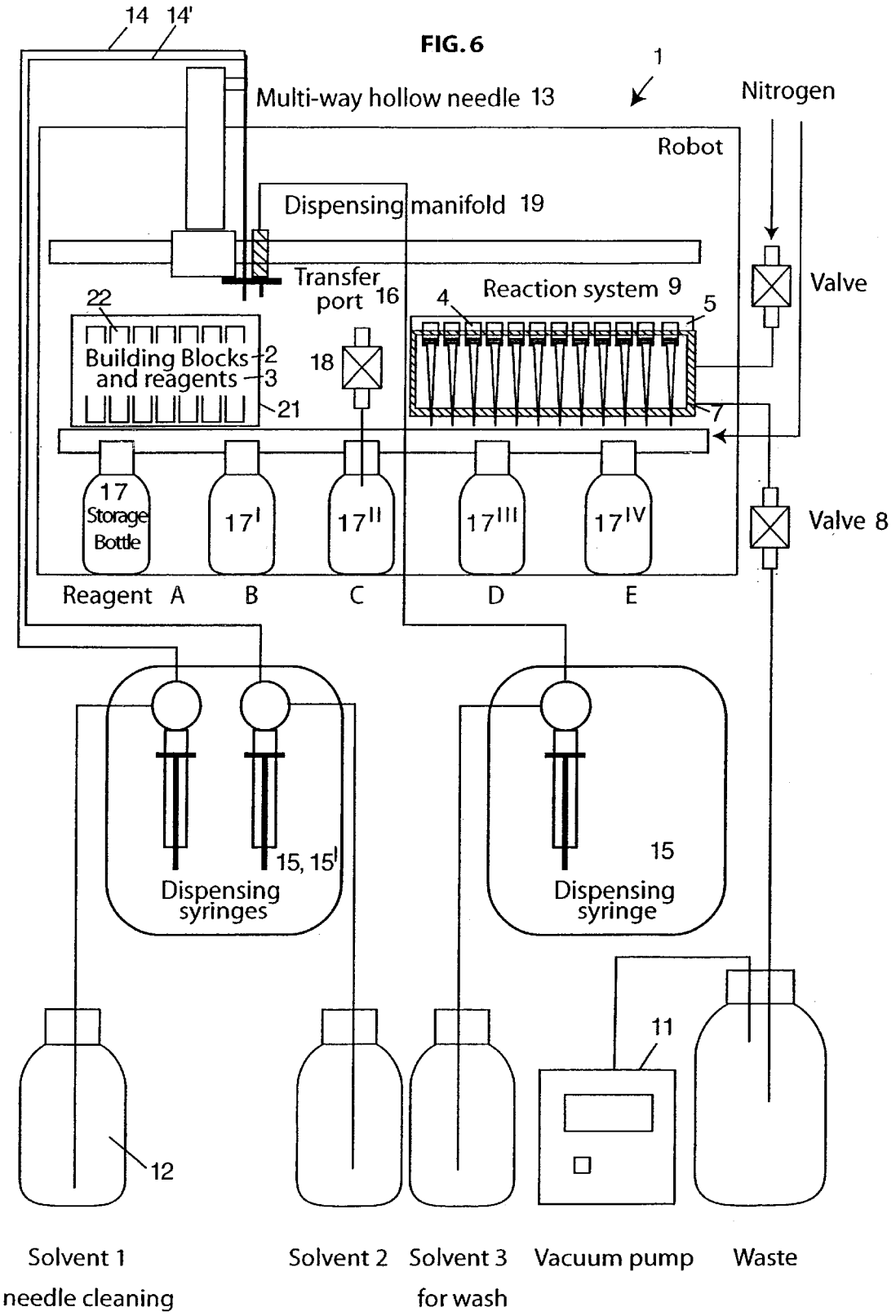

Double hollow needle having spring loaded

FIG. 9
Reactor module on 8x12 grid
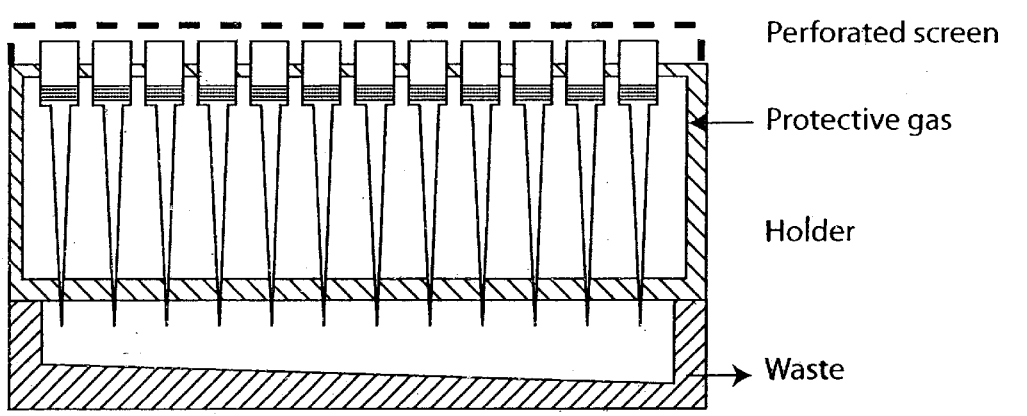
- Perforated screen
- Protective gas
- Holder
- Waste
Arrangement for removal and purification
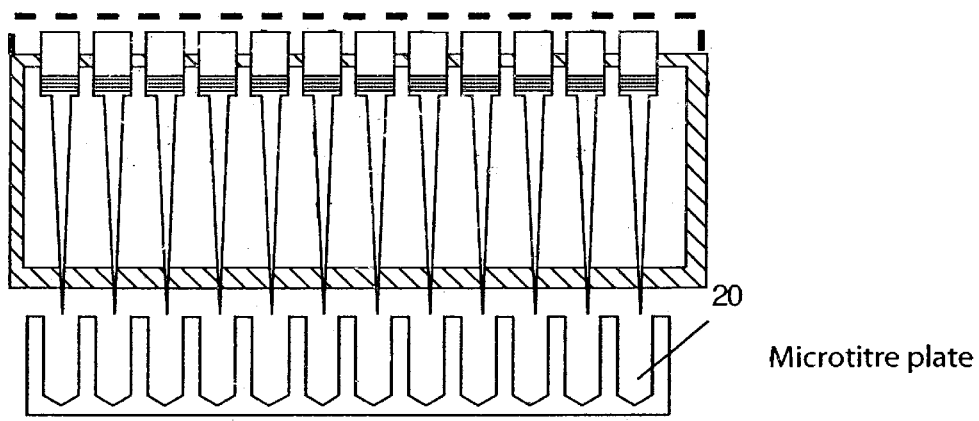
- Microtitre plate
Detailed View
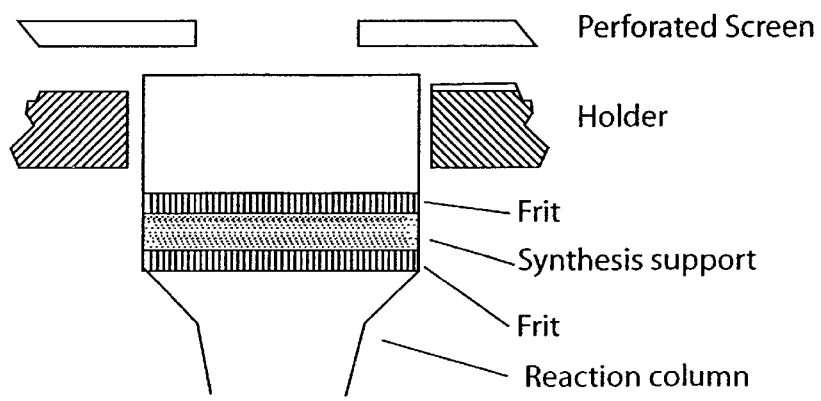
- Perforated Screen
- Holder
- Frit
- Synthesis support
- Frit
- Reaction column

AUTOMATED CHEMICAL SYNTHESIS APPARATUS

This application is a 371 of PCT/EP98/00901 filed Feb. 17, 1998 and claims priority to German patent application 197 06 089.7, filed Feb. 17, 1997.

The synthesis of polymeric biomolecules, such as oligonucleotides, peptides or non-natural analogues thereof, according to the principle of solid phase synthesis is an established technique (2).

Although multiple parallel synthesis of peptides in open reaction systems is part of the prior art (14, 15), oligonucleotides, for example, tend to be prepared individually. The principal problem in oligonucleotide synthesis lies in the extreme sensitivity to water of the phosphoramidite chemistry of the prior art (2). Automated oligosynthesis apparatuses are therefore closed systems and operate under protective gas. A published apparatus for the parallel synthesis of up to 96 oligonucleotides uses a reaction system that likewise is closed and, for the dispensing of reagents, a large number of valves (16). Conventional supports and manual work-up procedures are used therein.

The synthesis system according to the invention is therefore based on the idea of configuring synthesis, supports, anchor groups and work-up procedure for the simultaneous, fully automatic preparation of biomolecules. With the reagents' being distributed by means of a pipetting robot, the reaction columns can be arranged in a format that is suitable for further processing. In order also to be able to carry out a water- and air-sensitive synthesis protocol using a pipetting robot, it is necessary to take certain measures in terms of design. As an example of a possible solution, there will be described hereinbelow the principle of operation of the automated apparatus and the course of synthesis.

The automated apparatus can operate using conventional supports and reagents, but handling is simplified by specially modified, newly developed supports and anchor groups.

By adding on a special method for simultaneous purification and aliquotting, the quality of the products is improved and use is simplified.

The invention relates especially to the following embodiments: apparatus for automated simultaneous chemical synthesis and purification of a large number of products on solid phase, as well as support material and chemical building blocks for solid phase synthesis, characterised in that 1. a large number (from 10 to 1000, preferably 48 and a multiple thereof, preferably 400) of separate reaction vessels, which are open at the top and at the bottom, are provided in the form of channels or small columns, which are arranged in parallel in a block (FIG. 6) and which are removable either together or separately; the support material for the synthesis (solid phase) is placed in the channels/columns, either being arranged between two inert porous frit plates or, preferably, being itself in the form of a chemically modified frit or filter plate (FIG. 7), so that liquid media added from above are held in the reactor solely as a result of surface tension and wetting of the material;
2. the reactor/reactor block according to 1. is mounted on a trough connected to a vacuum pump by means of a switchable valve, and so the liquid media can be aspirated simultaneously from the reactors and the support materials contained therein;
3. the upper inlets to the reaction columns in the reactor block according to 1., which are covered by a perforated screen (baffle plate) mounted above them, can be flooded with inert gas (e.g. nitrogen, argon) and the flow of inert gas is optionally increased considerably during the aspirating procedure according to 2.; alternatively, the space above the reaction columns/channels can be selectively closed off by means of a second, displaceable perforated screen so that the reagents are blown out of the reaction columns/channels by pressurised inert gas;
4. chemical building blocks, reagents and solvents are distributed to the reaction vessels by an xyz-pipetting robot by means of electronically controllable dispensing syringes (dilutors) having one or more dispensing needles and optionally, in addition, one or more dispensing manifolds so that each reactor can be addressed individually;
5. the dispensing needle according to 4. is equipped with a plurality (at least two) of internal channels, which are connected to separate dispensing syringes, that is to say which can be filled separately, the ends of which channels meet only shortly before the outlet (FIG. 8) and so, when a plurality of reagents are being dispensed simultaneously, mixing occurs in the tip of the dispensing needle shortly before delivery, it being possible for a channel to be connected to the inert gas supply also and so the mixed volume can be expelled by means of a pulse of inert gas;
6. the dispensing needle according to 4. and 5. is mounted so as to be resilient along the longitudinal axis, so that it can set down on the support material or top frits in the reactor channels without damage and so can reliably deposit even extremely small volumes down to 1 nanoliter;
7. a large number (from two to one hundred, preferably 24) of chemical building blocks and reagents, where appropriate dissolved in suitable solvents, are provided in vessels which are sealed by means of septa and which are arranged in a reagent block separate from the reaction block;
8. the septum-sealed necks of the vessels in the reactor block according to 7., which are covered by a perforated screen (baffle plate) mounted above them, can be flooded with inert gas (e.g. nitrogen, argon);
9. using the dispensing needle according to 4. and 5., reagents can also be withdrawn from transfer ports, which are connected to storage bottles either directly or by means of switchable valves (FIG. 6) and the storage bottles are slightly pressurised with inert gas;
10. solvents and reagents can be distributed from solvent bottles by means of dispensing syringes or by pressurised inert gas and also by way of one or more dispensing manifolds according to 4. simultaneously to a plurality of reactors row by row;
11. the support material according to 1. forms a layer in the reactor channel, through which an even flow of the reagents and solvents applied from above passes solely under the action of gravity. According to the principle of solid phase synthesis (FIG. 2), which is part of the prior art, the individual products of each reactor are covalently bonded on the surface of the support material and are built up in parallel in steps by means of a succession of pipetting operations. During all the steps of synthesis (build-up reactions, repetitive protecting group removals and washing operations), the products remain covalently linked to the support material and are removed from the support material, and brought into solution, only in one or more final reaction steps;

12. the chemical building blocks (monomers) used for building up the products are coded as ASCII characters and so the products are described as a sequence of build-up reactions (monomer incorporation reactions) by means of ASCII words; the totality of all products for a synthesis program is consequently a list of ASCII words, which are converted by suitable software on a control computer into valve-switching operations, dispensing-syringe movement operations and robot arm movement operations, it being possible for each monomer incorporation to consist of a succession of several reaction steps and switching operations;

13. linking building blocks (linkers) suitable for covalently linking the products to the support material according to 11. are provided, which allow final removal of the products to take place selectively under mild conditions (FIG. 1). For the synthesis of oligomeric compounds, such as oligonucleotides, peptides etc., it is preferable to provide a "universal" linker, to which there can also be linked the building blocks of the first build-up reaction of the same chemical reaction type as that used for the further build-up reactions, as a result of which only one type of building block is needed for the entire synthesis of a class of compounds (e.g. only nucleoside-3'-phosphoramidites for the synthesis of 3'-OH-oligonucleotides);

14. in the final removal reactions, the linker according to 13. is preferably firstly converted into a labile, but still intact, form (safety-catch linker), which is then cleaved by means of mild chemical treatment, preferably a pH change. Using a linker of that type, the covalently bonded products can be purified of chemical reagents in a simple manner by means of automatic washing operations on the support material and only at the very end eluted from the reactors into an arrangement of collection vessels which is complementary to the reactor arrangement (FIG. 9);

15. the target products of the syntheses are provided with a group that can be used as an affinity label, by means of which the target products can be bound to a corresponding affinity phase. By that means the products eluted from the reactors are purified in an arrangement of affinity columns which is complementary to the reactor arrangement (FIG. 9). By means of simple automated washing or removal operations, the target products are subsequently eluted from the affinity columns into an arrangement of collection vessels which is complementary to the reactor arrangement;

16. the binding capacities of the affinity columns according to 15. are limited in such a manner that, even when synthesis yields differ, an identical minimum amount of target product is bound and eluted per reactor, so that all the products of a multiple synthesis are obtained in equimolar amounts.

Arranged on the working surface of an exemplary pipetting robot are:
  a stand for derivative solutions, optionally under protective gas with septum
  reagent withdrawal ports, in this case switchable by valves
  reagent bottles under protective gas
  a holder for reaction columns.

The reaction columns consist of plastics tubes having inserted frits, which enclose the actual synthesis support and which fix the support in a defined position or have themselves been derivatised as a support. In this instance, commercially available pipette tips have been used as tubes. Alternatively, it is possible to use an injection-moulded component in the form of a unit, comprising individual cavities having filter frits (e.g. from PolyFiltronics, Rockland, Mass., USA).

The upper portion of the reaction system can be flushed with protective gas. A perforated screen in the form of a cover can prevent the ingress of air even when the volume flow is low.

A vacuum can be applied to the lower portion of the reaction system for the purpose of aspirating the reagents. An alternative arrangement uses a second, displaceable perforated screen, by which means the holes can be closed off when necessary and the reaction columns cleared by blowing through pressurised protective gas.

For the purpose of dispensing reagents, the robot is provided with a hollow needle having at least two independent channels. The channels meet only very shortly before the outlet. By means of connected motor-operated dispensing syringes it is possible for reagents to be taken up separately and delivered simultaneously. In the simplest case, the hollow needle consists of two concentrically arranged tubes (see Figure). The hollow needle is mounted so as to be resilient along the longitudinal axis so that even extremely small volumes down to 1 $\mu$l can be deposited on the support frits without damaging them.

In order to speed up synthesis, one or more of the reagents and solutions can also be dispensed by means of a distributing manifold. The distributing manifold is either also supplied by a dispensing syringe or it is arranged to be connected, by means of valves, to one or more pressurised storage containers. The distributing manifold dispenses reagents, always simultaneously, to a row of reaction columns. Synthesis then consists of a series of program-controlled transfers of reagents and solvents from the storage containers to the reaction columns. The synthesis procedure and type of reagents are, in principle, known and are part of the prior art.

Synthesis commences with the sequences' being set out in the form of a list of ASCII character strings in the controlling computer program. The synthesis procedure is defined as a sequence of operations specifying the reagents, the volumes to be transferred in each case and the reaction times to be adhered to. An example of a procedure program is given in the appendix.

The apparatus is then equipped with the necessary reagents and synthesis supports. Conventional supports according to the prior art need to be assigned to the individual sequences, because the first building block has to be attached separately outside the apparatus. A simplification is achieved by using the universal support according to the invention, in which case the first building block is coupled inside the automated synthesis apparatus. The chemistry relating thereto is described in the enclosure.

Synthesis typically begins with a washing step, which is preferably performed by means of the distributing manifold. For the purpose of removing the solvents, the aspirating valve is switched for a specified time and a vacuum is applied to the lower portion of the reaction system. During that time the flow of protective gas to the upper portion is increased considerably in order to substantially prevent the ingress of outside air. Then, typically, a solution for removing the temporary protecting groups, e.g. trichloroacetic acid in acetonitrile, is distributed by means of the hollow needle. The needle is firstly moved into the closed transfer port, which seals tightly against the outside of the needle. The valve is then opened and the reagent is drawn up into one of the channels of the needle. Usually, more than the required amount is drawn up because mixing can occur in the boundary region in the tubing between the needle and dilutor. The boundary region between the liquids is usually defined by an air bubble also drawn up. The valve is re-closed, and the needle moves to the first reaction column. The needle is set down on the top frit or on the support itself, as appropriate, and the first aliquot of reagent is delivered. Movement to the other positions is performed analogously.

The excess in the tubing is then discarded and the hollow needle is rinsed.

In the case of reagents that have to be mixed, for example in order to activate the monomeric building blocks, firstly one of the reagents is drawn up as described. The second (and, where appropriate, further) reagent is then aspirated into the second channel of the hollow needle. In order that the first aliquot delivered will have the correct mixture, some of the excess is discarded at the beginning by actuating both dilutor syringes simultaneously. The needle then moves to the positions specified by the program, sets down on the frit and dispenses the reaction mixture by simultaneously actuating the dilutor syringes. That process is the crucial step in synthesis: by keeping the reagents apart until they are dispensed onto the support, the reaction that competes with the coupling-hydrolysis caused by traces of water—is delayed. By that means, synthesis in a reaction system that is in fact open to the atmosphere is indeed possible, contrary to the prevailing opinion of those skilled in the art.

The further synthesis procedure consists of a sequence of similar steps using a variety of reagents set out by the program procedure.

Synthesis is followed by the known deprotection and removal of the products from the support, e.g. by incubating with concentrated ammonia solution.

Alternatively, a "safety-catch linker" according to the invention can be used, which remains intact when the protecting groups are removed and is merely brought into a more labile state. All reagents and by-products can therefore be washed out before the synthesis products are removed from the support in a separate step. Using the safety-catch linker makes synthesis work-up considerably easier because ammonia and by-products can be separated off more easily than was previously possible.

Work-up is also made easier as a result of the arrangement of the reaction vessels in a standard format, e.g. that of microtitre plates.

Because the reactions during synthesis never run to completion, it is entirely usual, if not always necessary, to purify the products. For that purpose, the method described by Blöcker and Frank (9A) can be proposed. Alternatively, it is also possible to use other known affinity purification procedures, e.g. by means of the interaction of biotin and avidin (17A, 17B).

Most applications demand a relatively accurately determined amount of synthesis product. In the case of oligo-nucleotides for sequencing reactions, that amount is only a fraction of the synthesis yield. In this case the yield for all the synthesis batches can, according to the invention, be made uniform by using a limiting amount of affinity matrix. The amount of affinity matrix is well defined and in each case considerably more labelled synthesis product is applied than corresponds to the binding capacity.

The amounts of synthesis product subsequently eluted are then approximately equal (Attachment 9B). The combination of affinity purification and aliquotting is new and saves elaborate concentration measurements.

As a result of the modular construction of the automated synthesis apparatus, it is possible to combine synthesis, removal, purification and aliquotting in one apparatus. When the method according to EP 0 174 525 is used, an affinity support made from a polymeric material, e.g. polystyrene, polyethylene or modifications thereof, can be used. The material can be so selected that it is inert with regard to the synthesis of protecting group removal. It can then even be arranged as a frit below the synthesis support, which would greatly simplify work-up compared with the prior art.

A) Chemical Pre-conditions for Highly Parallel DNA Synthesis

The working principle of the envisaged multiple automated synthesis apparatus provides for a grid of simple small reactors, in which small porous membrane frits constitute the support material for the synthesis. In each reactor the scale of synthesis should be optimally adapted in line with the application as sequencing primer and be in the range from 1 to 10 nanomol. The concept for chemical derivatisation of the support material for use in the step-wise building-up of oligonucleotides is illustrated in FIG. 1A.

Firstly, detection reactions of adequate sensitivity were established in order to be able to follow the individual derivatisation steps quantitatively on the nanomolar scale:

for hydroxy functions: tritylation with dimethoxytrityl chloride in pyridine followed by acidic detritylation with dichloroacetic acid in dichloroethane and photo-metric determination of the dimethoxytrityl cation;

for amino functions: staining with the anionic dye bromophenol blue in dimethyl-formamide, followed by basic dissociation and photometric determination of the bromophenol blue anion.

A very wide variety of commercially available polyolefin-based membrane materials were then tested for suitability. Depending on their manufacture, those materials already exhibit non-specific oxidative ageing of the surface with hydroxy, ketone, aldehyde and carboxy groups (FIG. 2). A procedure was therefore developed which firstly "cleans" that polymeric surface by reduction and then, by means of selective and readily controllable oxidation, generates exclusively the hydroxy groups required in this case (FIG. 3). By that means it is now possible to produce frit material having a predetermined functionality which is suitable for use for oligonucleotide synthesis. A large number of chemical reactions using those and other hydroxylated materials (e.g. cellulose papers) were carried out in order to attach suitable "spacers" and "linkers" (FIG. 4). The frits so obtained have been successfully used in a commercial automated synthesis apparatus for oligonucleotide synthesis (FIG. 5) and are now available for tests in the reactor module of the new automated apparatus.

Ideally it should be possible to use the support material (support-spacer-linker), prepared according to FIG. 1A, universally for every oligonucleotide sequence so that individual configuration of the synthesis grid is not necessary. This is not provided by conventional loading in a separate reaction with 3'-nucleoside succinates (each sequence requires one of the four different loaded supports). For that reason, a universal "linker" should be employed, on which oligonucleotide synthesis can be started directly using a first nucleotide building block. The concept of intramolecularly cleavable phosphodiesters according to Köster and Heyns (Tetrahedron Letters 1972, 1531) and Gough et al. (Tetrahedron Letters, 1983, 5321) was utilised for that purpose and suitable linker building blocks were produced and anchored to the support material (FIG. 4, compound type 3). In model syntheses it has been shown successfully that the concept works.

A further aspect of the envisaged synthesis technology is the integrated parallel purification and storage of the oligonucleotides. By using a "safety-catch" linkage on the support surface to be developed specifically for that purpose, it will be possible to carry out support-bound deprotection and purification. For that purpose a chemical concept was developed that constitutes a modification of the universal linker (FIG. 4, compound type 3). Corresponding model compounds were prepared, by means of which the feasibility of the concept was checked with a successful outcome.

B) Experimental Version of a DNA Synthesis Machine

A first version of the apparatus was constructed on the basis of the original concept, the necessary control software being produced externally (FIGS. 6 to 9).

C) Examples of Quantification (and Purification) of the Oligonucleotides Produced Depending on the sequence of bases of the synthesised oligonucleotides, different overall yields are obtained. The following method makes it possible to obtain a uniform defined amount of the varous oligonucleotides, the oligonucleotides being purified at the same time.

1. A hydrophobic polyolefin powder (PE, PP, or PTFE) serves as the material for the quantification. Defined amounts of the powder (e.g. 20 mg, 10 mg, 5 mg or 2.5 mg) are introduced into sterile filter tips (Eppendorf) or into appropriate tips fitted with frits. The powder is prepared by washing with acetonitrile (3×250 $\mu$l in each case) and then with 1M triethylamine acetate buffer (TEAA) (3×250 $\mu$l in each case).
2. The oligonucleotides synthesised using the PRIME96 synthesis robot, which oligonucleotides still contain the hydrophobic trityl protecting group, are removed from the support. Solution A is obtained in this manner (in this example: 200 $\mu$l of 33% $NH_3$ solution). The resulting solution A is diluted 1:1 with water and applied to the prepared columns and slowly forced through with the aid of a syringe.
3. Rinsing with 2.5% $NH_3$ (aq) (3×250 $\mu$l in each case) and water (3×250 $\mu$l in each case) is carried out.
4. The trityl protecting group is now removed using 2% trifluoroacetic acid (aq) (3×250 $\mu$l in each case). After 5 minutes, rinsing with water (3×250 $\mu$l in each case) is carried out.
5. Quantified and purified oligonucleotide is then eluted using 20% acetonitrile (aq) (3×250 $\mu$l in each case).

EXAMPLE 7.2 OD (approx. 40 nmol) of a mixed 18-mer were applied

| mg of quantification resin* | applied eluate ($OD_{260}$) | TFA eluate ($OD_{260}$) | end product ($OD_{260}$) | recovery rate (%) |
|---|---|---|---|---|
| 2.5 | 5.5 | 0.9 | 0.427 | 94 |
| 5 | 5.22 | 0.9 | 0.968 | 98 |
| 10 | 4.3 | 0.7 | 1.93 | 95 |
| 20 | 3.32 | 0.4 | 2.68 | 88 |

Micropure, BTI Technologies, San Raffael, Calif., USA
As a "rule of thumb", this series of tests shows that approx. 1 nmol of oligonucleotide is bound per mg of quantification resin. Quantification is based on the fact that a defined amount of oligonucleotide, which initially is still tritylated, is bound per mg of the purification material used. Because the amount of oligonucleotide synthesised in each case using the PRIME96 is always greater than the amount that can be bound by the purification material, quantification is possible by simple means.

D) Example of Support Material for Solid-phase Synthesis Using a Synthesis Robot Innovative Concept Our innovative synthesis concept is based on the fact that the various reaction solutions adhere to a solid support solely as a result of capillary forces and are able to react therewith. Unreliable and expensive valve systems can therefore be dispensed with.

That can be achieved, on the one hand, by placing a conventional support material between two inert frits. Developing a support that already possesses a defined porous structure so that it can then be functionalised is, however, even better. The latter method has the following advantages:

- commercially available support material having a defined macroporous pore diameter
- reproducible manufacture
- large surface area
- good through-flow characteristics
- defined structure
- mechanically stable
- basic material substantially chemically inert, only the surface is derivatised We have here developed a new support system of that kind, the possibility of using known methods for functionalisation having been excluded by, especially, the porous structure of the starting material.

Functionalisation of polyolefin frits (using polyethylene and polypropylene as examples)

1) Reduction

As a result of the manufacturing process (sintering), commercially available polyolefin frits are already oxidised (carboxy, carbonyl, hydroxy groups). In order to produce a uniform starting material in this case, reduction is firstly necessary. For that purpose, 50 mmol of $LiAlH_4$ are introduced into a three-necked flask fitted with a reflux condenser and 50 ml of dry diethyl ether are added dropwise. 1 g of PE frits are then added and heated under reflux for 6 hours. Then the excess of $LiAlH_4$ is firstly hydrolysed using aqueous ether and the precipitate is re-dissolved using 10% $H_2SO_4$. Washing is carried out using 3×100 ml of water, then 2×100 ml of 10% $NaHCO_3$, 3×100 ml of water again and 1×100 ml of MeOH, and drying is carried out under a high vacuum.

2) Direct Hydroxylation 1 g of the reduced polyolefin frits are introduced into a solution of 10 ml of $H_2O_2$ (30% aq) and 100 ml of trifluoroacetic acid. Heating under reflux is carried out for from 15 to 60 minutes.

Depending on the reaction time, loadings of from 250 nmol of OH/g (15 minutes) to 5 $\mu$mol of OH/g (60 minutes) are obtained. (The loading with OH groups was determined by means of DMT coupling.)

The method used here for hydroxylation has hitherto been described in the literature only for alkanes and cycloalkanes.

The porous hydroxylated supports so prepared are universally suitable for use for all solid phase syntheses.

3) Coupling of the First Building Block (Start Nucleoside) to the Support

Example 1

(See also FIG. 4, Attachment 1)

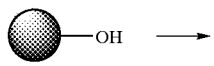

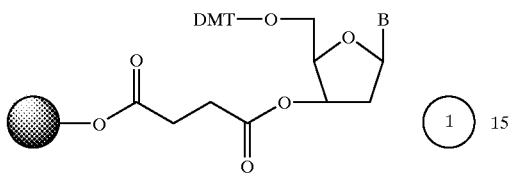

20 μmol of DMT-dT$^{an}$-Succ are dissolved in 100 μl of DMF, and 31 μmol of N,N'-diisopropylcarbodiimide (DICD) are mixed in. After 10 minutes, 25 μmol of methylimidazole are mixed in and 60 mg of the hydroxylated polyolefin frits (see above for preparation) are added under nitrogen. After 24 hours at 25° C., the frits are washed successively with DMF, pyridine and methylene chloride.

Example 2

Insertion of a Spacer (See also FIG. 4, Attachment 1)

Insertion of the hexamethylene spacer:

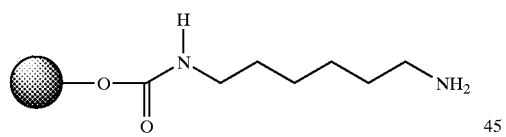

180 mg of hydroxylated polyolefin frits dried under a high vacuum (see above for preparation) are shaken in 5 ml of a 0.3M solution of 1,1'-carbonyldiimidazole in DMF under nitrogen for 6 hours at RT. The frits are then rinsed 3 times with 50 ml of DMF each time and then shaken in 5 ml of a 0.3M solution of 1,6-diaminohexane in DMF for 18 hours. The frits are then washed with DMF, methanol, acetone and ether and dried under a high vacuum at RT.

Coupling of the start nucleoside:

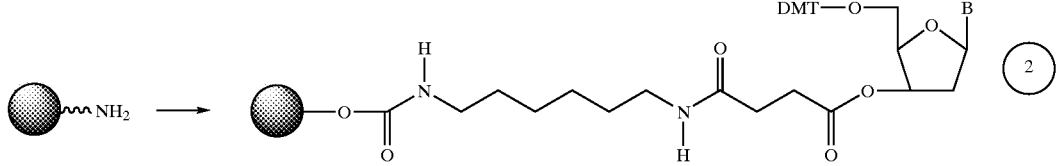

Procedure analogous to Example 1, but without methylimidazole.

Functionalisation of PTFE

PTFE frits are treated with sodium naphthalide and then hydrolysed. Hydroxylated PTFE frits are obtained even at this stage. By subsequent hydroboration, the concentration of hydroxy groups on the support can be further increased by a considerable amount.

Further support material (tested in the PRIME96)

- cellulose (see Attachment 12)
- commercial support material (Pharmacia) in the form of powder between two frits (see Attachment 11)

E) Examples of Linkers

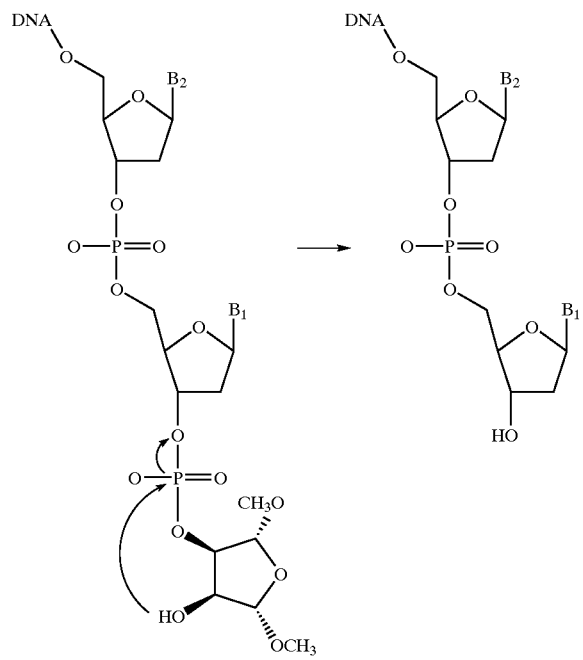

H. Köster and K. Heyns (1972)^, Tetrahedron Letters 1972, 1531

G. R. Gough, M. J. Brunden and P. T. Gilham (1983), Tetrahedron Letters 1983, 5321

Scott, P. Hardy, R. C. Sheppard and M. J. McLean (1994): in. Solid Phase Synthesis (R. Epton, Ed.), Mayflower Worldwide Ltd., Birmingham, UK, p. 115

New universal linkers for the synthesis of oligonucleotides on solid phase (phosphoramidite chemistry):
The following linker systems were prepared and tested:

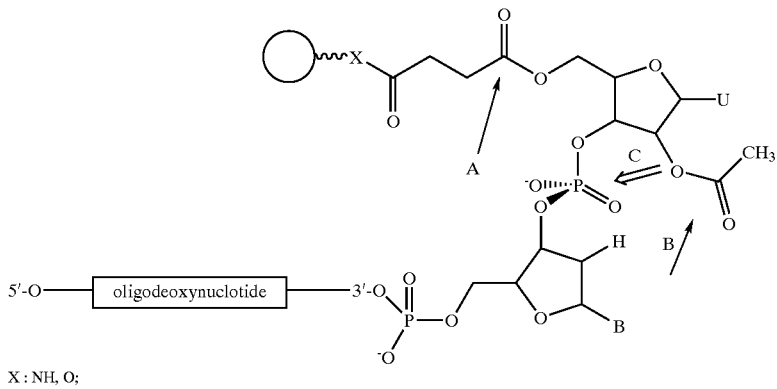

X : NH, O;

Type 1a: Removal from the support and simultaneous hydrolysis of the linker molecule:
  A and B: rapid ester hydrolysis by $NH_3$ or LiOH;
  C: slow phosphodiester cyclisation by acid or base;

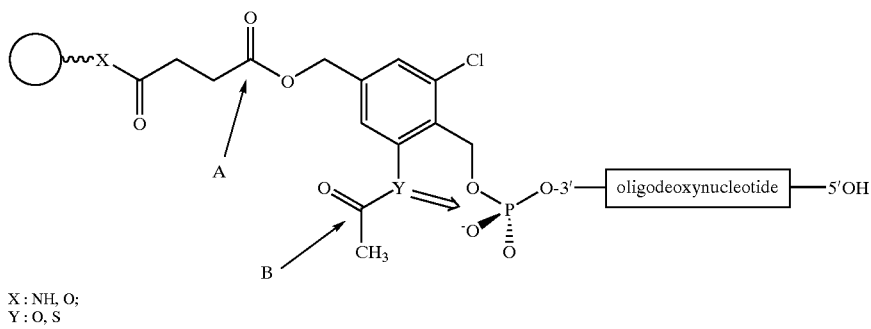

X : NH, O;
Y : O, S

Type 1b: Removal from the support and simultaneous hydrolysis of the linker molecule:
  A and B: rapid ester hydrolysis by $NH_3$ or LiOH;
  C: accelerated phosphodiester cyclisation by acid or base;

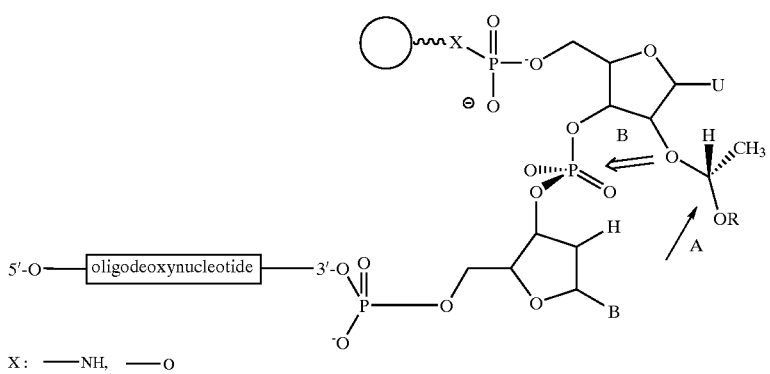

X : —NH, —O

Type 2: Irreversible anchoring of the linker molecule to the solid phase; removal of the linker by 2-stage mechanism;
  A: rapid acid acetal hydrolysis (dil. $AcOH/H_2O$):
  B: slow phosphodiester cyclisation (LiOH);

New universal linkers for oligonucleotide synthesis (phosphoramidite chemistry):
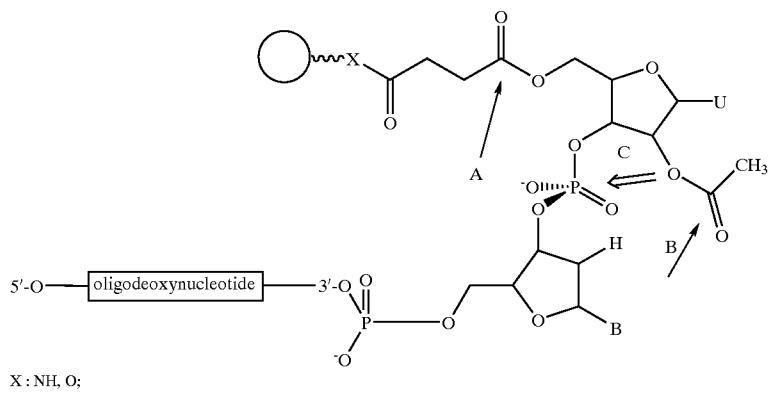
X : NH, O;
Type 1a: Removal from the support and simultaneous removal of the linker building block:
A and B (rapid ester hydrolysis, $NH_3$ or LiOH);
C (slow phosphodiester cyclisation, $NH_3$ or LiOH);
Synthesis:
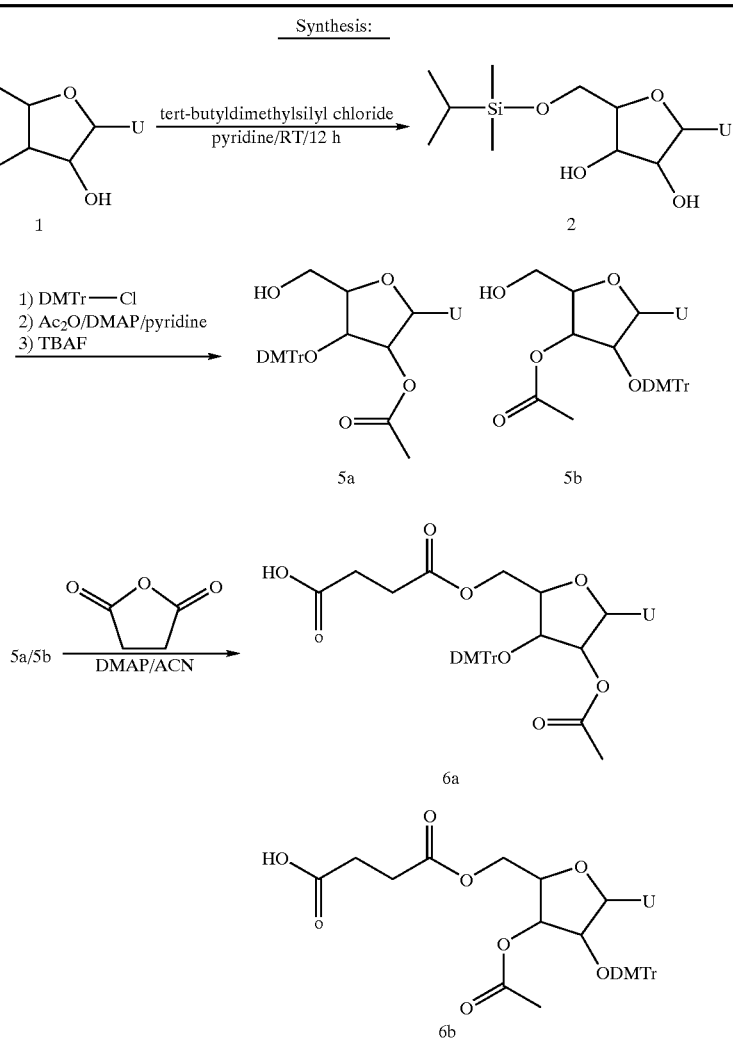

-continued
Optional:
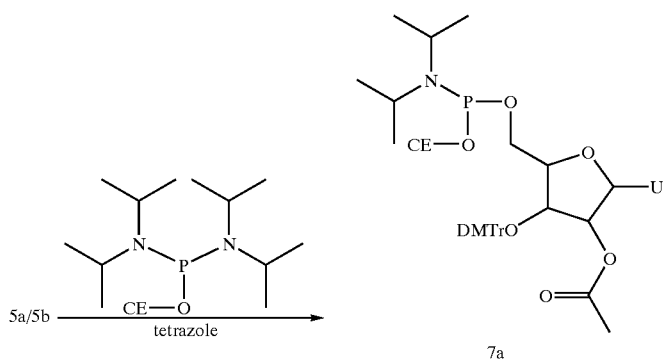
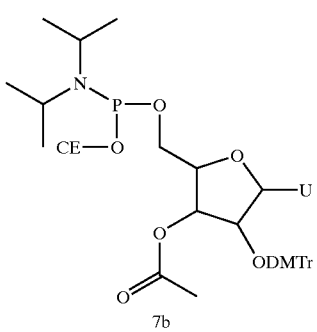
CE = —CH$_2$CH$_2$CN
| Structure | Empirical formula Molecular weight | Test number | $^1$H | $^{31}$P | EA | UV | MS |
|---|---|---|---|---|---|---|---|
| TBDMSiO—U, OH, OH | C$_{15}$H$_{26}$N$_2$O$_6$Si [358.47] | V201 | ▽ | ○ | ○ | ○ | 358.47 [ESI⊖] |
| TBDMSiO—U, ODMTr, OH  + 2′, 3′-regio. | C$_{36}$H$_{44}$N$_2$O$_8$Si [660.84] | V202P2 | ▽ | ○ | ○ | ○ | 660.4 [FAB⊖] |
| TBDMSiO—U, OAc, ODMTr  + 2′, 3′-regio. | C$_{38}$H$_{46}$N$_2$O$_9$Si [702.88] | V203P1 | ▽ | ○ | ○ | ○ | 702.3 [FAB⊖] |
| HO—U, OAc, ODMTr | C$_{32}$H$_{32}$N$_2$O$_9$ [588.61] | V201.P1 V204.P2 | ▽ | ○ | ○ | ○ | 588.4 [FAB⊖] |

-continued
| | | | | | | | |
|---|---|---|---|---|---|---|---|
| 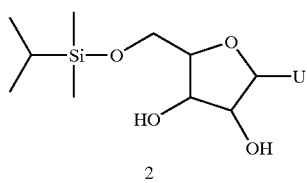 | $C_{36}H_{36}N_2O_{12}$ [688.69] | V205 | ▽ | ○ | ○ | ○ | 688.37 [ESI⊖] |
| 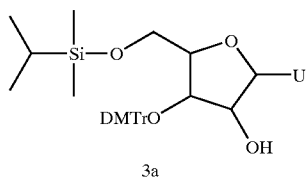 | $C_{57}H_{62}N_2O_{10}Si$ [963.21] | V202.NP | ▽ | ○ | ○ | ○ | 962.6 [ESI⊖] |
| 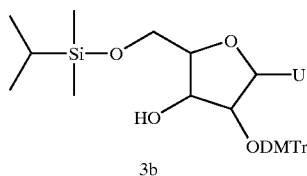 | $C_{41}H_{49}N_4O_{10}P$ [788.84] | V267 | ▽ | ▽* | ○ | ○ | 789.4 [ESI⊖] |
Key:
TBDMSi = tert-butyldimethylsilyl-
Ac = acetyl-
▽* = 150.4219/150.1271/148.1382/146.9553
Succ. = succinic acid ester
CE = 2-cyanoethyl-
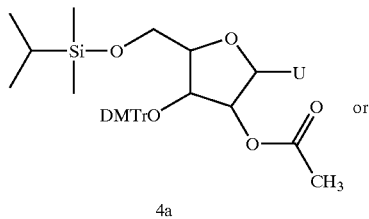
2
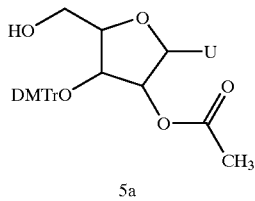
3a     3b
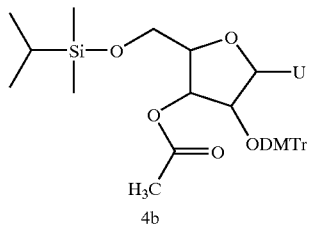 or 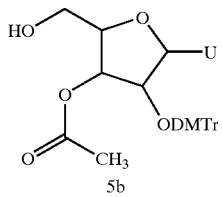
4a     5a
4b     5b

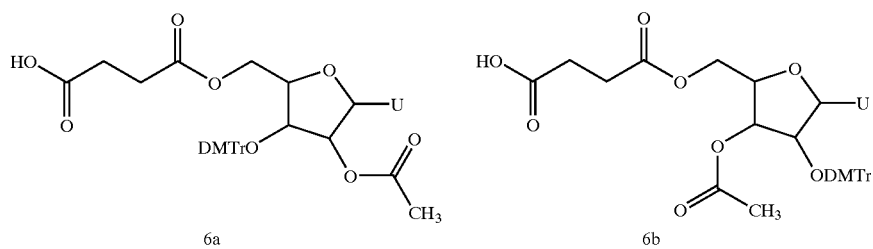
6a 6b
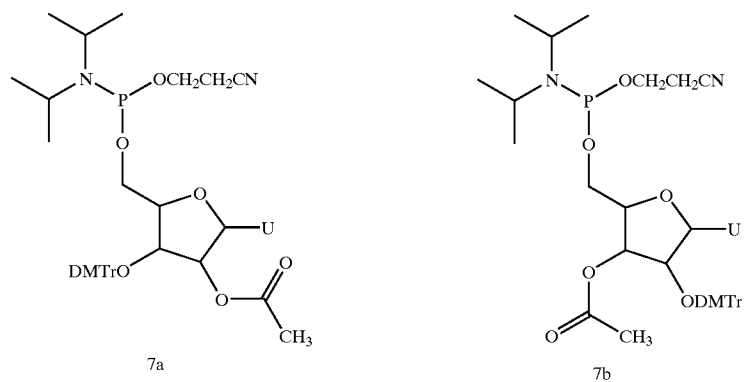
7a 7b
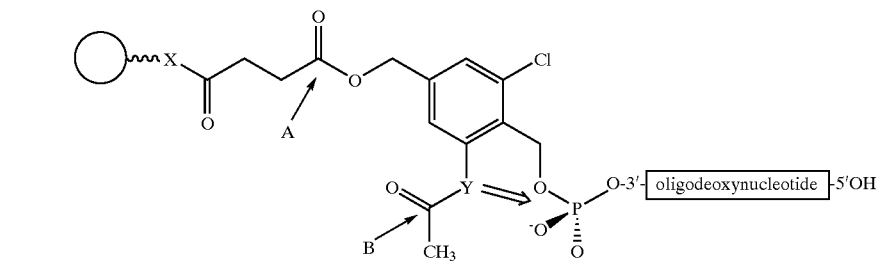
X: NH, O;
Y: O, S
Type 1b: Removal from the support and simultaneous removal of the linker molecule:
A and B (rapid ester hydrolysis, NH$_3$ or LiOH);
C (accelerated phosphodiester cyclisation by phenolate or thiophenolate formation with NH$_3$ or LiOH)
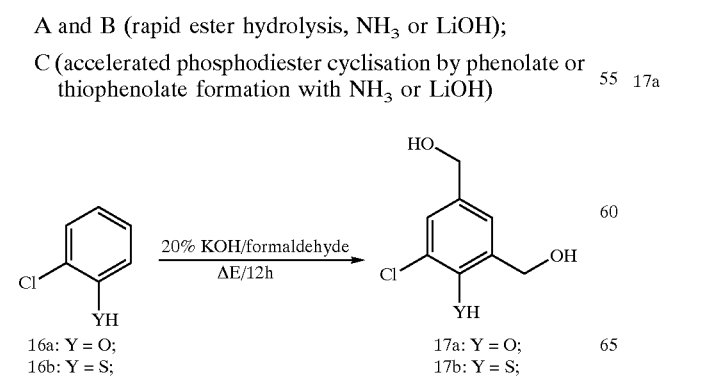
16a: Y = O; 17a: Y = O;
16b: Y = S; 17b: Y = S;
-continued
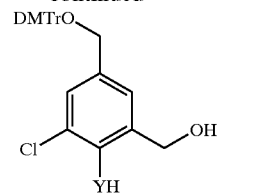
18a
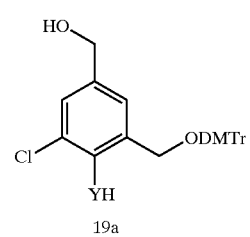
19a

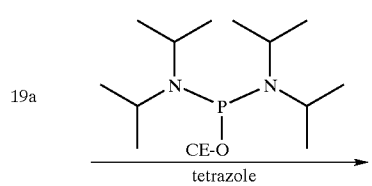
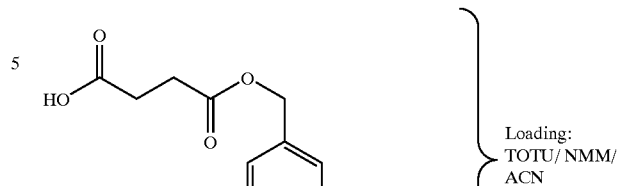
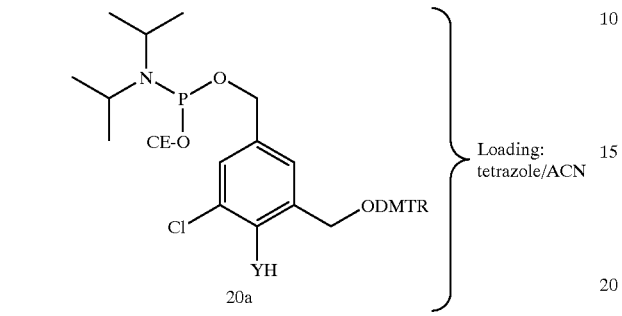
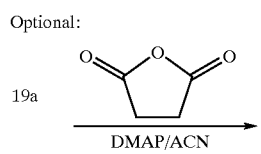
Capping:
After loading of the support material, acylation is carried out.
(Capping) of the phenolic HO or HS function by reaction with acetic anhydride or pivaloyl chloride with DMAP catalysis;
| Structure | Empirical formula Molecular weight | Test number | $^1$H | $^{31}$P | EA | UV | MS |
|---|---|---|---|---|---|---|---|
| 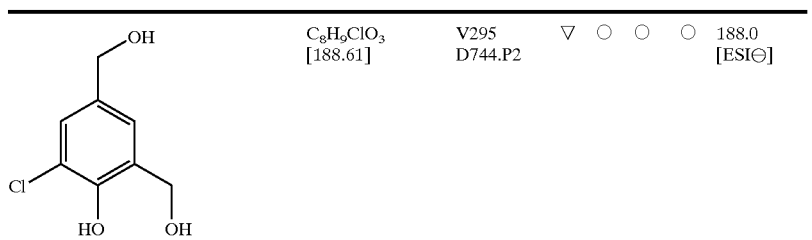 | $C_8H_9ClO_3$ [188.61] | V295 D744.P2 | ▽ | ○ | ○ | ○ | 188.0 [ESI⊖] |
| 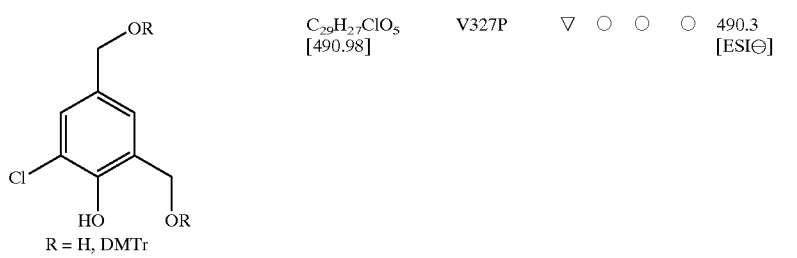 R = H, DMTr | $C_{29}H_{27}ClO_5$ [490.98] | V327P | ▽ | ○ | ○ | ○ | 490.3 [ESI⊖] |
| 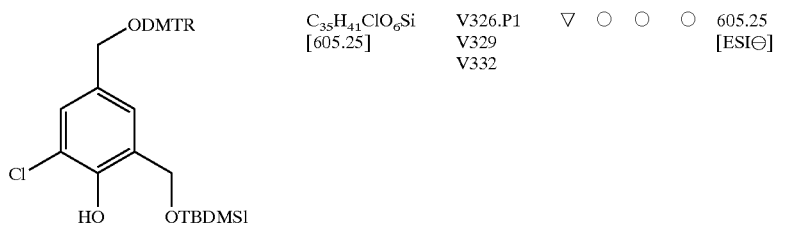 | $C_{35}H_{41}ClO_6Si$ [605.25] | V326.P1 V329 V332 | ▽ | ○ | ○ | ○ | 605.25 [ESI⊖] |

-continued
| Structure | Formula | Code | | | | | Mass |
|---|---|---|---|---|---|---|---|
| 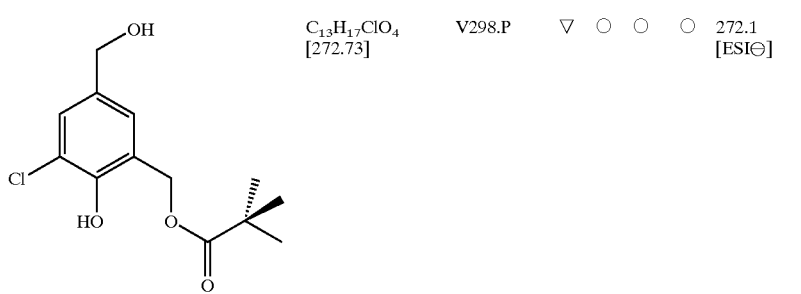 | C$_{13}$H$_{17}$ClO$_4$ [272.73] | V298.P | ▽ | ○ | ○ | ○ | 272.1 [ESI⊖] |
| 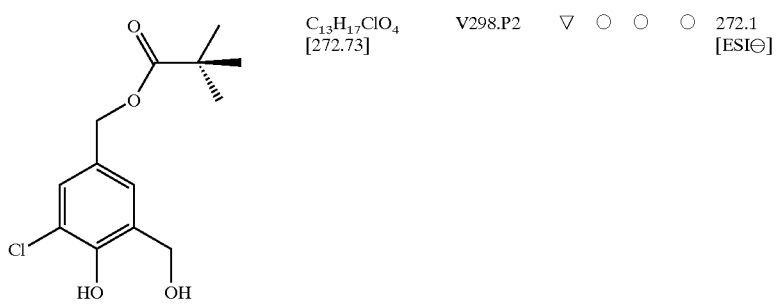 | C$_{13}$H$_{17}$ClO$_4$ [272.73] | V298.P2 | ▽ | ○ | ○ | ○ | 272.1 [ESI⊖] |
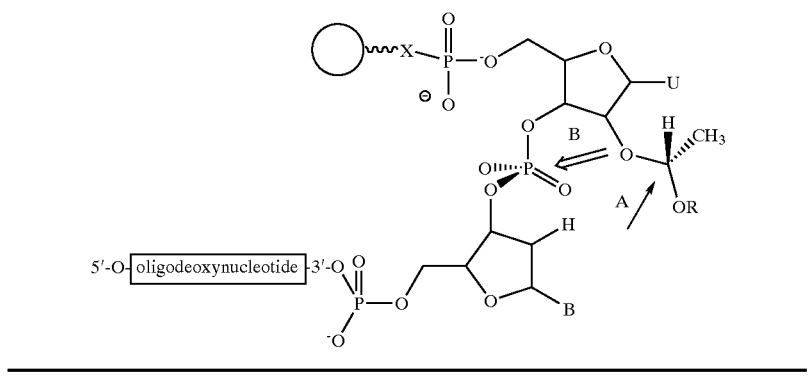
X: —NH, —O
Type 2: Irreversible anchoring of the linker molecule to the solid phase; removal of the linker by 2-stage mechanism
A: rapid acid acetal hydrolysis (AcOH);
B: slow phosphodiester cyclisation (LiOH);
Synthesis
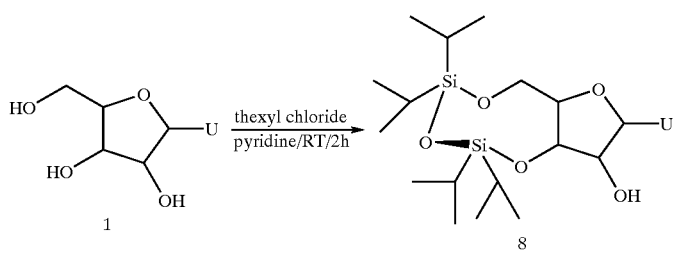

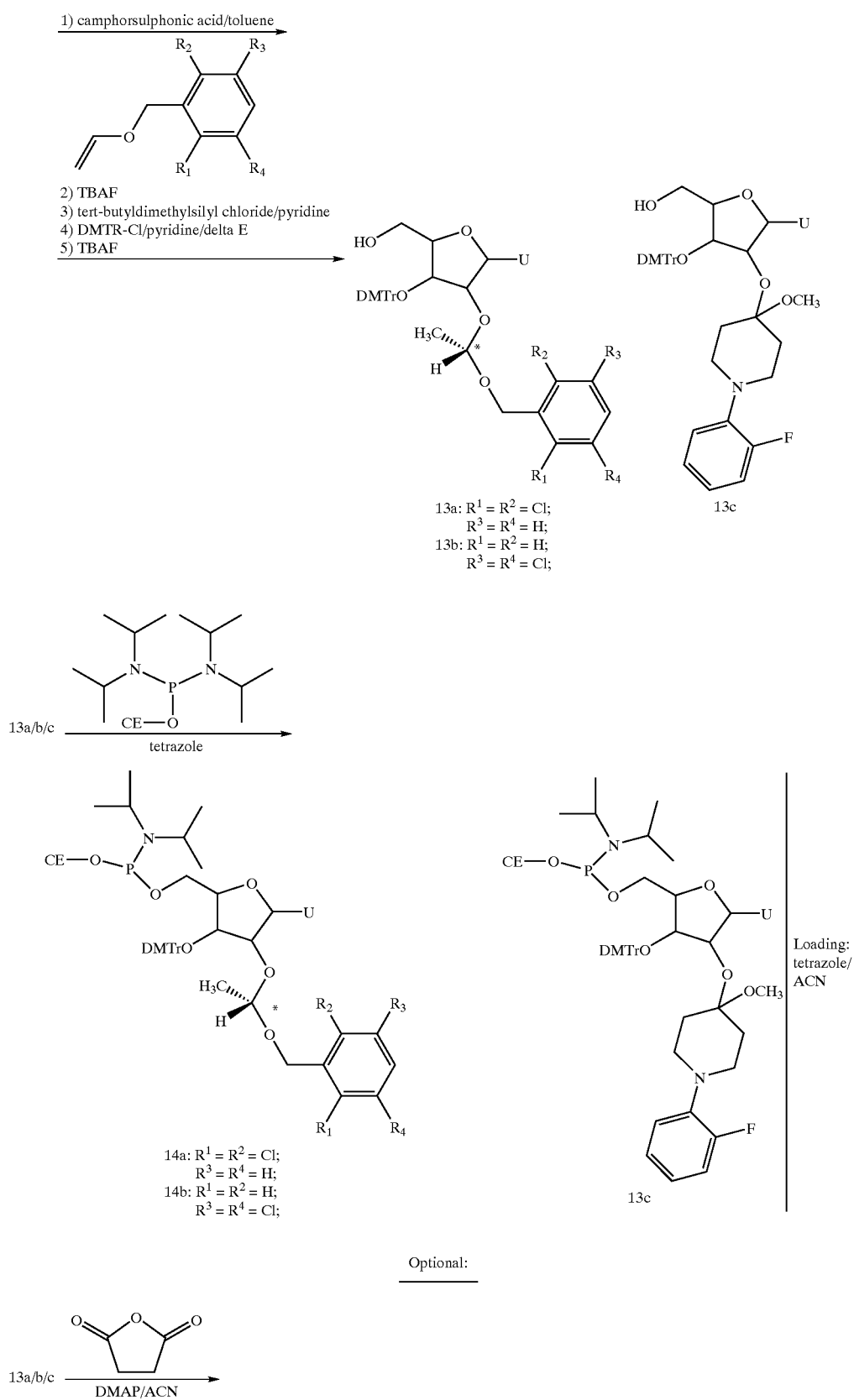

-continued
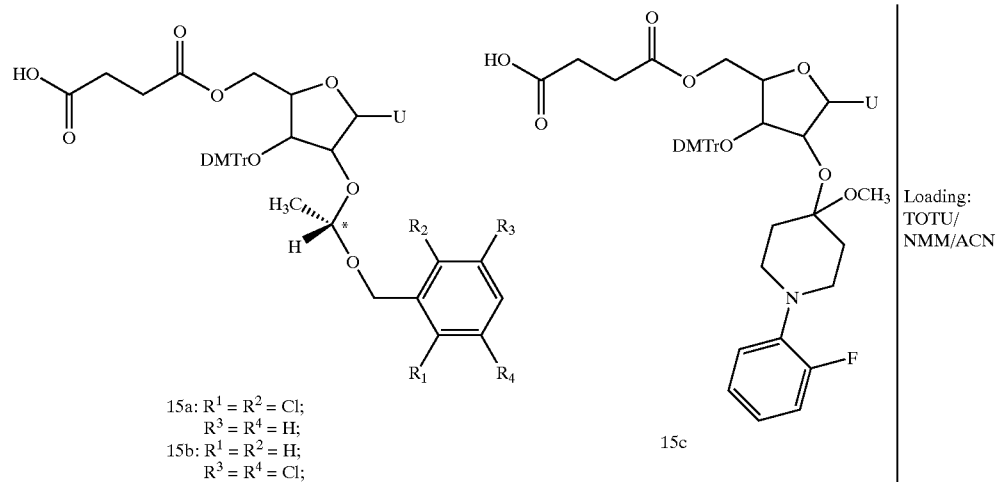
15a: $R^1 = R^2 = Cl$; $R^3 = R^4 = H$;
15b: $R^1 = R^2 = H$; $R^3 = R^4 = Cl$;
15c  Loading: TOTU/ NMM/ACN
| Structure | Empirical formula Molecular weight | Test number | $^1H$ | $^{31}P$ | EA | UV | MS |
|---|---|---|---|---|---|---|---|
| 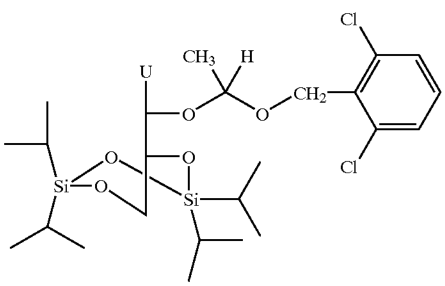 | $C_{30}H_{46}Cl_2N_2O_8Si_2$ [689.72] | V53 | ○ | ○ | ○ | ○ | ○ |
| 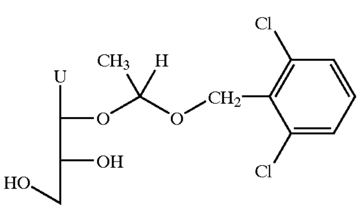 | $C_{18}H_{20}Cl_2N_2O_7$ [448.28] | V62 | ▽ | ○ | ○ | ○ | ○ |
| 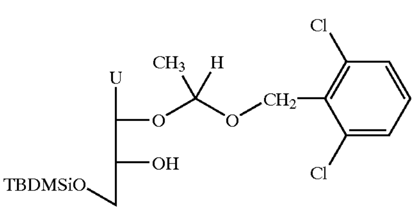 | $C_{24}H_{35}Cl_2N_2O_7Si$ [562.54] | V64 | ▽ | ○ | ○ | ○ | ○ |
| 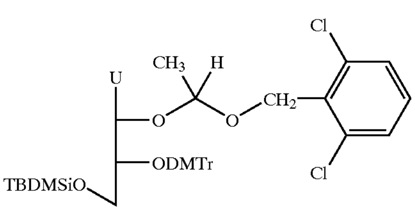 | $C_{45}H_{53}Cl_2N_2O_9Si$ [864.91] | V67 | ▽ | ○ | ○ | ○ | ○ |

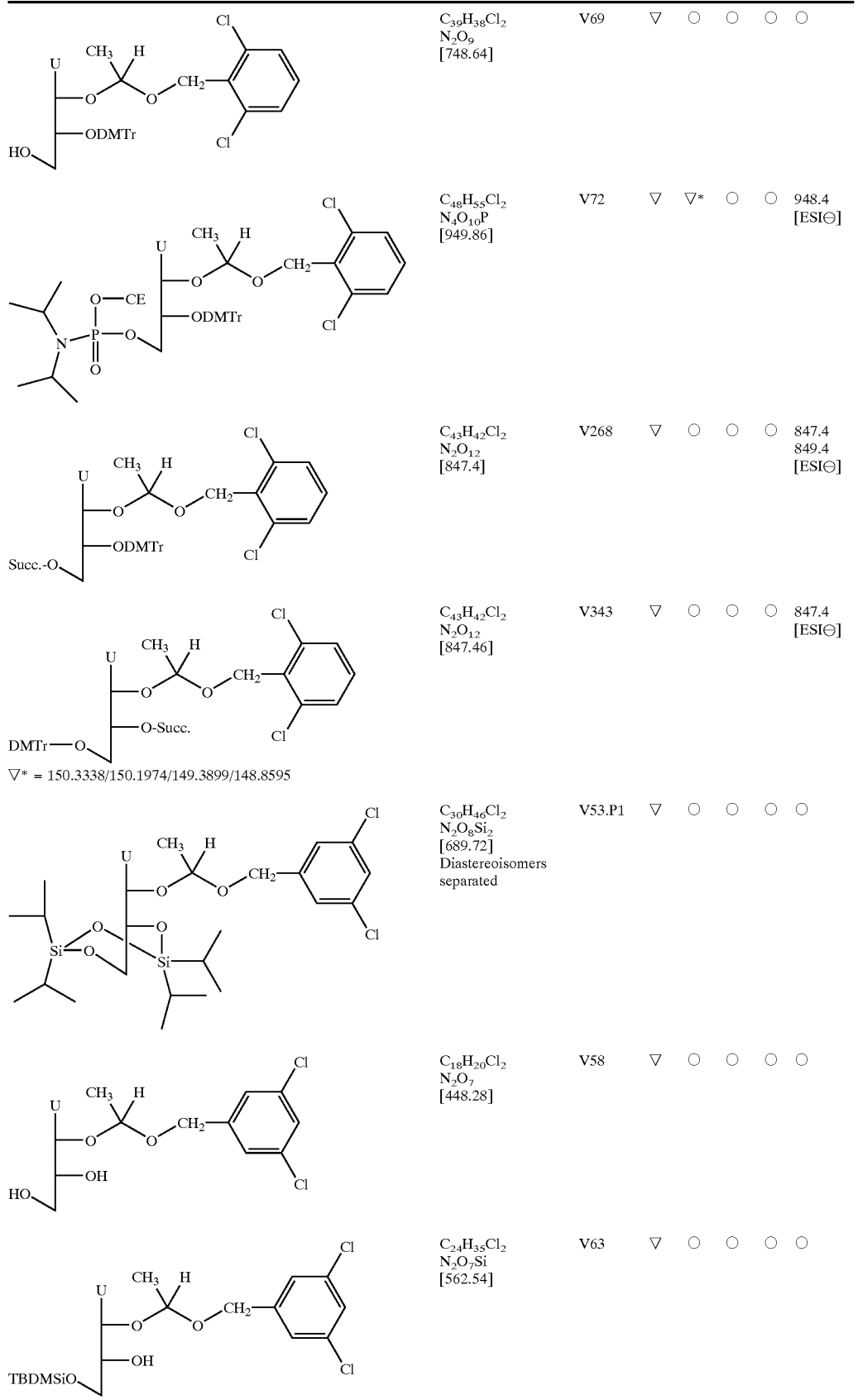

-continued

| Structure | Empirical formula Molecular weight | Test number | $^1H$ | $^{31}P$ | $^{19}F$ | UV | MS |
|---|---|---|---|---|---|---|---|
| (structure with U, CH₃, H, ODMTr, TBDMSiO, OCH₂-3,5-dichlorobenzyl) | C₄₅H₅₃Cl₂N₂O₉Si [864.91] | V66 | ▽ | ○ | ○ | ○ | ○ |
| (structure with U, CH₃, H, ODMTr, HO, OCH₂-3,5-dichlorobenzyl) | C₃₉H₃₈Cl₂N₂O₉ [748.64] | V68 | ▽ | ○ | ○ | ○ | ○ |
| (phosphoramidite structure with U, CE, ODMTr, 3,5-dichlorobenzyl) | C₄₈H₅₅Cl₂N₄O₁₀P [949.86] | V73 | ▽ | ▽* | ○ | ○ | 948.6 [ESI⊖] |
| (cyclic phosphate dimer structure with U, T, TBDMSi, CE, ODMTr) | [1219.4] | V90 | ▽ | ▽# | ○ | ○ | 1219.4 [ESI⊖] |

▽* = 150.5141/150.1323/149.9590/149.6179
▽# = −1.1891/−2.2436/−2.3141/−?
▽ = analysis carried out; result confirms structure
○ = analysis not carried out

| Structure | Empirical formula Molecular weight | Test number | $^1H$ | $^{31}P$ | $^{19}F$ | UV | MS |
|---|---|---|---|---|---|---|---|
| (U, OFPMP, OH, HO) | C₂₁H₂₆FN₃O₇ [451.45] | Crua-chem Scot-land | ▽ | ○ | ▽¹ | ○ | ○ |
| (U, OFPMP, ODMTr, TBDMSiO) | C₂₇H₄₀FN₃O₇Si [565.71] | V49 V70 | ▽ | ○ | ▽² | ○ | ○ |
| (U, OFPMP, ODMTr, TBDMSiO) | C₄₈H₅₈FN₃O₉Si [868.09] | — | ▽ | ○ | ▽³ | ○ | ○ |

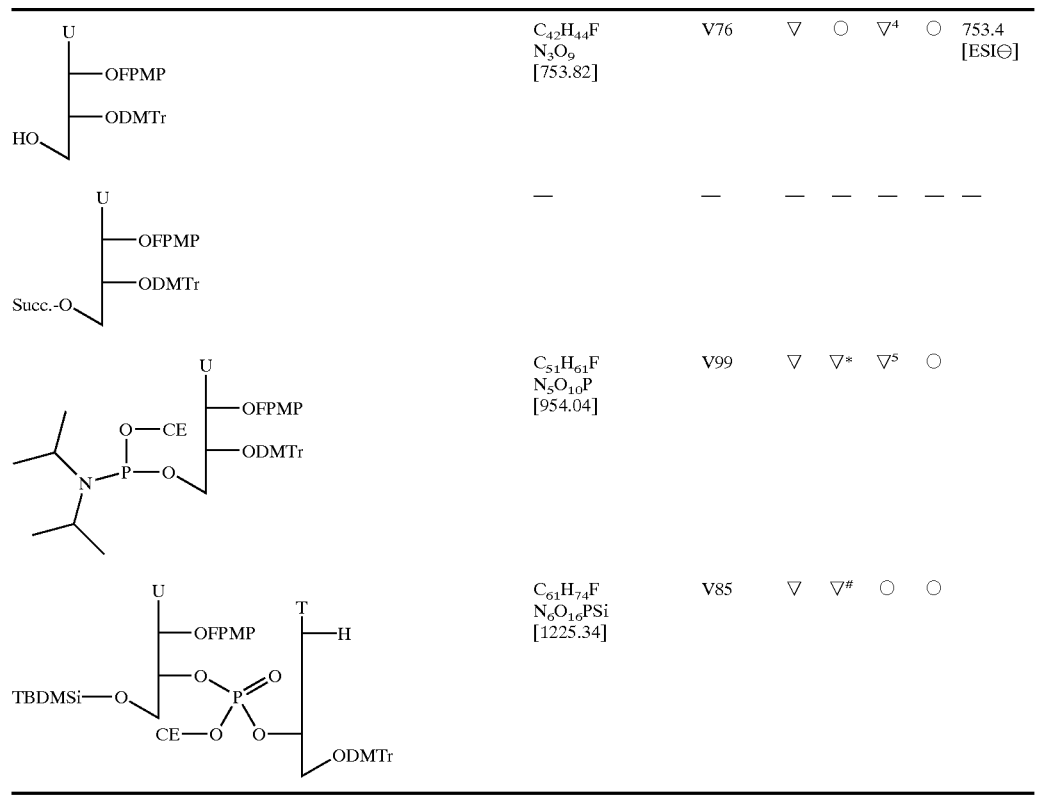
$\nabla^1 = -123.2279$
$\nabla^2 = -123.2503$
$\nabla^3 = -123.4784$
$\nabla^4 = -123.5$
$\nabla^5 = -123.5164/123.6284$
$\nabla^* = 149.3809/148.6848$
$\nabla^\# = -2.3711/-2.4548$
$\nabla$ = analysis carried out; result confirms structure
$\bigcirc$ = analysis not carried out
F) Examples of Porous Frit Plates
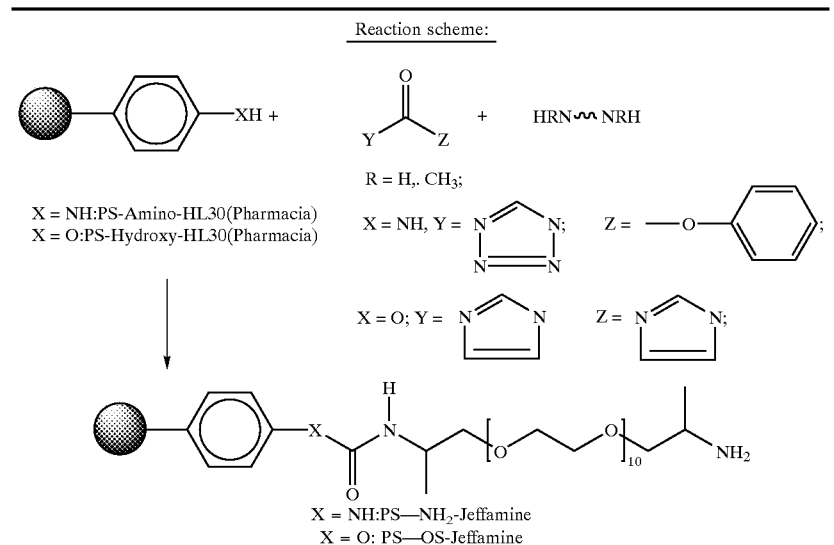

-continued

| Name | —X | Support material | Test number | Loading number | Capping | Loading result |
|---|---|---|---|---|---|---|
| PS—NH$_2$—Jeffamine | —NH | PS-Amino-HL30 | — | V224A | — | — |
| Conditions: 106 mg (15.2 µmol) support; 18.5 mg (97.9 µmol) PCT ||||||| 
| Activation: 18 h/RT/1 ml AcN; 1.75 mmol Jeffamine 500; 24 h/RT + 5 h/60° C. ||||||| 
| PS—NH$_2$—Jeffamine | —NH | PS-Amino HL30 | — | V232A | — | — |
| Conditions: 510 mg (73 µmol) support; 163 mg (862 µmol) PCT ||||||| 
| Activation: 17 h/RT/1 ml AcN; 0.525 mmol Jeffamine 500; 2.5 h/RT + 5.5 h/60° C.1 ||||||| 
| PS—NH$_2$—Jeffamine | —NH | PS-Amino HL30 | — | V288B3 | — | BPB: 60 µmol/g |
| Conditions: 1.024 g (145 µmol) support; 200 mg 1.053 mmol) ||||||| 
| Activation: 24 h/RT/20 ml AcN; 400 mg act. support +300 µl Jeffamine 500/24 h/60° C. ||||||| 
| Capping: 10 ml DMF; 3 ml pyridine; 0.5 ml Ac$_2$O; 15 mins/RT; ||||||| 
| PS—OH—Jeffamine | —O | PS-Hydroxy-HL30 | — | V232B | — | BPB: 72 µmol/g |
| Conditions: 357 mg support; 137 mg CDI (844 µmol) ||||||| 
| Activation: 17 h/RT/5 ml AcN; 525 µmol Jeffamine 500; 2.5 h RT + 5.5 h/60° C. |||||||

Advantages of the Spacer Molecule:
- After activation of the amino function, the unreacted functions on the support surface can be capped with acetic anhydride. Possible subsidiary reactions due to vicinal hydroxy functions (intramolecular ring closure and removal from the support during ammonia treatment) are thereby avoided.
- The loading can be ascertained by staining the basic amino functions which have not been fully reacted, using the bromophenol blue (BPB) test after activation, capping and aminolysis.
- Using bi-functional aminopolyglycol spacers (e.g. Jeffamine 500) makes the hydrophobic support surface more hydrophilic. That can have a beneficial effect on the reaction yields in oligomer synthesis (for example, the electrostatic charge is reduced; the hydrophilic spacer arms extend further into polar solvents etc.).

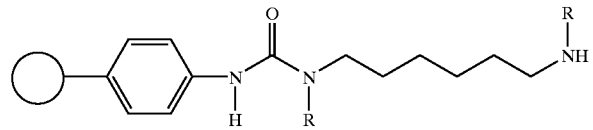

| Name | —X (—R) | Support material | Test Number | Loading Number | Capping | Loading result |
|---|---|---|---|---|---|---|
| PS—NH$_2$—Amino-hexane | —NH (—H) | PS-Amino-HL30 | — | 277 | — | BPB: 102 µmol/g |
| Conditions: 500 mg (71.5 µmol) support; 50 mg PCT (264 µmol); 24 h/RT; 600 µmol 1,6-diaminohexane 4.0 ml AcN/DMF (1/1) 60° C./12 h ||||||| 
| Capping: Ac$_2$O DMF pyridine (0.5/5/2 ml) 500 mg DMAP 10 mins./RT ||||||| 
| PS—NH$_2$—Amino-hexane | —NH (—H) | PS-Amino-HL30 | — | V288.B4 | — | BPB: 188 µmol/g (?) |
| Conditions: 1.024 g (144 µmol) support; 200 mg PCl (1053 µmol); 24 h/RT; 600 mg alkt. support + 420 mg 1,6-diaminohexane 12 h/60° C. ||||||| 
| PS—NH$_2$—Methyl-amino-hexane | —NH | PS-Amino-HL30 | — | V312 | — | BPB: 97 µmol/g |
| Conditions: 1.031 g (145 µmol) support; 125 mg PCT (0.661 mmol); ||||||| 
| Activation: 3 h/RT/10 ml AcN; 300 mg N,N'-dimethyl-1,6-hexanediamine; 16 h/60° C. ||||||| 
| Capping: Ac$_2$O DMF pyridine (0.5/5/2 ml) 500 mg DMAP 15 mins./RT |||||||

-continued

Reaction scheme:

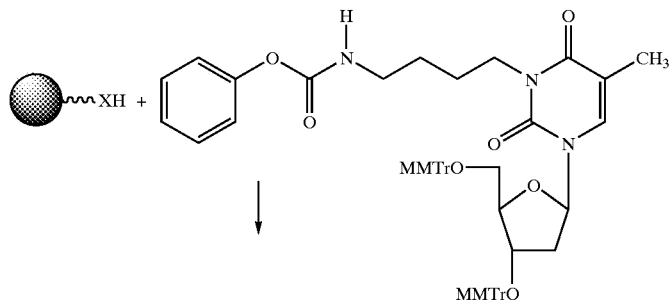

↓

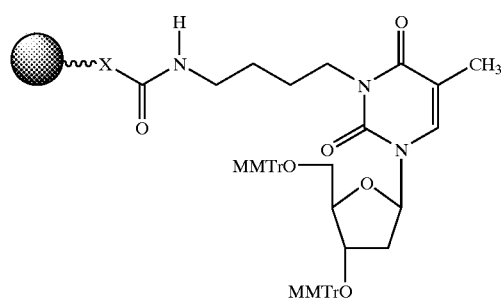

| Name | —X | Support material | Test Number (spacer) | Loading Number | Capping | Loading result |
|---|---|---|---|---|---|---|
| PS—NH$_2$—Thymidine-3',5'-MMTr | NH | PS-Amino-HL30 | V210 | V225 | | MMTr. 27 μmol/g |
| Conditions: 118 mg (17 μmol) support; 8.2 mg (8.4 μmol); 15 h/60° C./1.5 ml AcN | | | | | | |
| Capping: Ac$_2$O DMF pyridine (0.1/1.0/0.5 ml) 100 mg DMAP 10 mins./RT | | | | | | |
| PS—NH$_2$—Jeffamine-thymidine-3',5'-MMTr | NH | PS—NH$_2$—Jeffamine | V210/ V232A | V240A | — | MMTr. 15 μmol |
| Conditions: 86 mg V232A 7.8 mg (8.0 μmol) V210; 25 h/60° C./1.0 ml AcN | | | | | | |
| PS—OH—Jeffamine-thymidine 3',5'-MMTr | O | PS-OH—Jeffamine-thymidine-3',5'-MMTr | V210/ V232B | V240B | — | MMTr. 18 μmol |
| Conditions: 60 mg V232B 7.7 mg (7.9 μmol) V210; 25 h/60° C./1.0 ml AcN | | | | | | |

Reaction scheme:

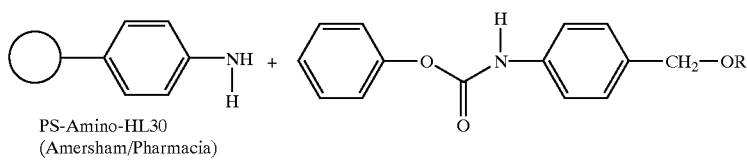

PS-Amino-HL30
(Amersham/Pharmacia)

R = H, DMTr;

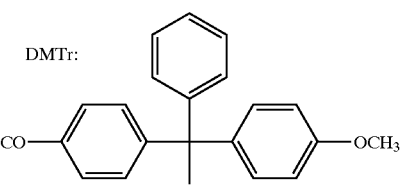

DMTr:

↓

-continued

[Chemical structure: polymer support—phenyl—NH—C(=O)—NH—phenyl—CH₃—OR]

| Name | —R | Support material | Test Number | Loading Number | Capping | Loading result |
|---|---|---|---|---|---|---|
| PS—NH₂—Benzyl alcohol-OH | —H | PS-Amino-HL30 | D744 | 310 | | Indirectly via BPB 110 μmol/g |
| Conditions: 500 mg (71.5 μmol) support; 80 mg (329 μmol = 4.6 molar equivalents) 20 h/60–70° C. in 5 ml CH₃CN | | | | | | |
| Capping: DMAP Ac₂O CH₃CN 30 mins. RT | | | | | | |
| PS—NH₂—Benzyl alcohol-ODMTr | —DMTr | PS-Amino-HL30 | V366-P1 | | | — |
| Conditions: | | | | | | |

Advantages of the spacer molecule
- A possible subsidiary reaction due to vicinal hydroxy functions is avoided.
- The loading can be ascertained by staining the basic amino functions which have not been fully reacted, using the bromophenol blue (BPB) test, especially when R=H. In the case of the tritylated variant, the loading can be determined either by means of BPB or, after capping, by means of the trityl value.
- In the case of loading with a 3'-O-phosphoramidite, there are formed, instead of the acid-labile phosphoric acid amidates, the more stable phosphoric acid diesters (W. Bannwarth; Helv. Chim. Acta, Volume 71, 1517 (1988). That is advantageous with respect to the use of safety-catch 2'-O-acetal linkers (see Attachment 5)!

BRIEF DESCRIPTION OF THE DRAWINGS

FIG. 1A: Molecular modules for the solid phase synthesis of oligonucleotides. P=polymeric support material; X=chemical function for anchoring (—O— or —NH—); linker=unit for reversibly anchoring the first nucleotide building block; $N_{1,2}$=nucleotide building blocks

FIG. 2: Reactivity of the surfaces of various PE materials in the tritylation/detritylation test; red.=cleaned by reduction FIG. 3: Controlled hydroxylation of PE material

FIG. 6: Diagram of the automated chemical synthesis apparatus.

FIG. 7: Diagram of the components of the reactor and reactor arrangement.

Figure 1B:
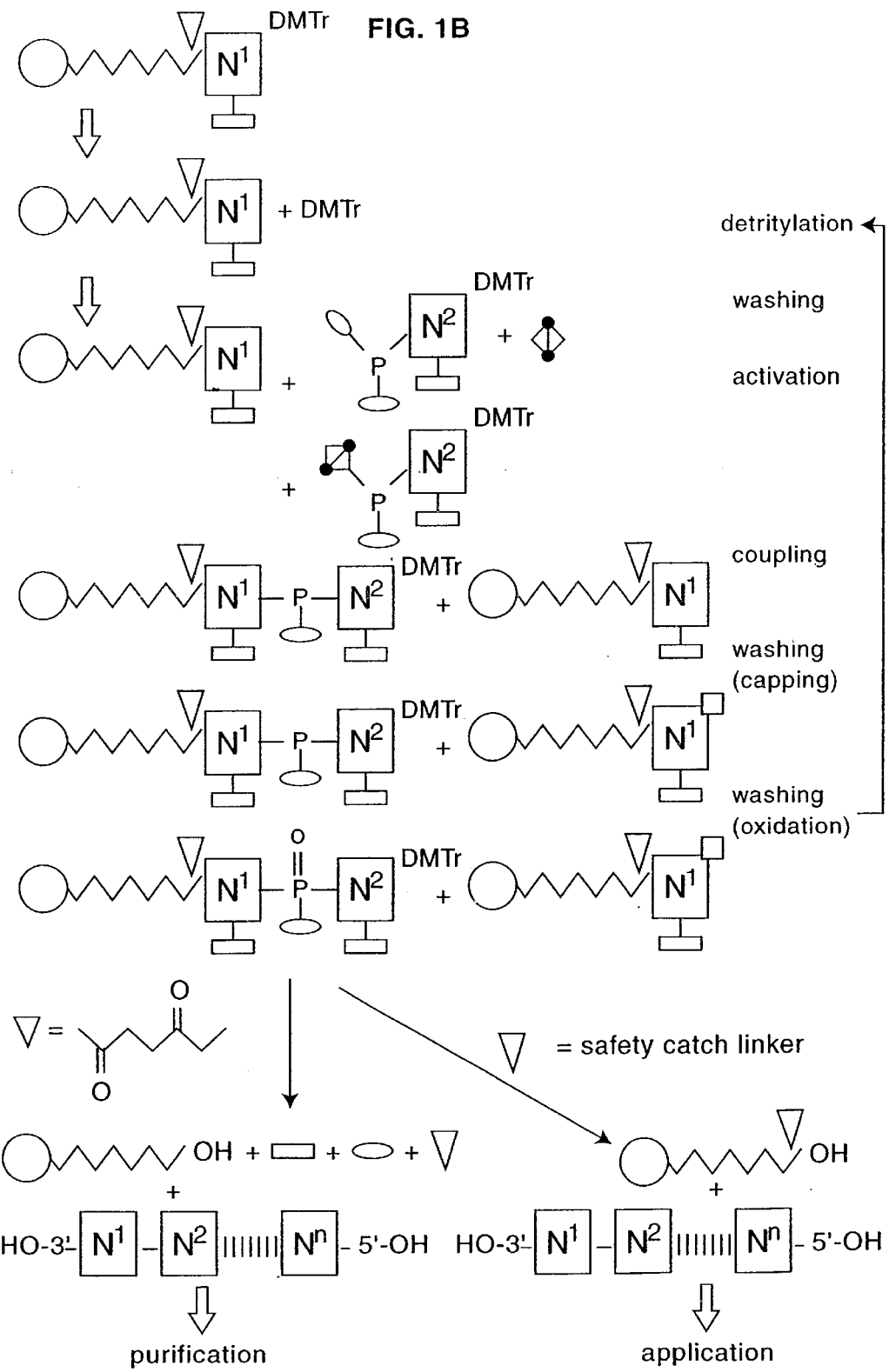
FIG. 1B: Schematic representation of the "Synthesis principle".
Figure 4:
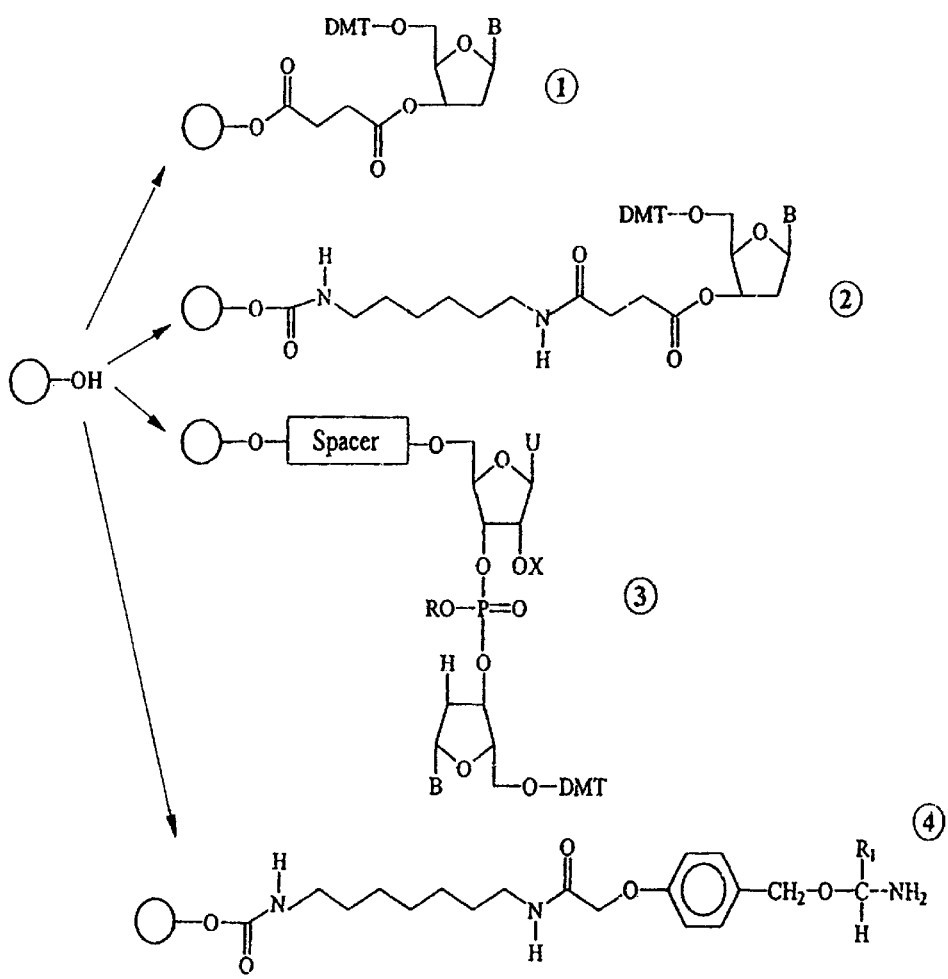
FIG. 4: Examples of the modular synthesis supports outlined in FIG. 1. The starting material is hydroxylated polymer; 1 and 2 are conventional support loadings with 3'-nucleoside succinates without and with a spacer; 3 is the concept of the universal linker (X=acyl) and the "safety-catch" linker (X=orthogonal protecting group), the riboU-nucleoside representing the linker and not being incorporated into the oligonucleotide; 4 is a support material loaded for peptide synthesis
Figure 5:
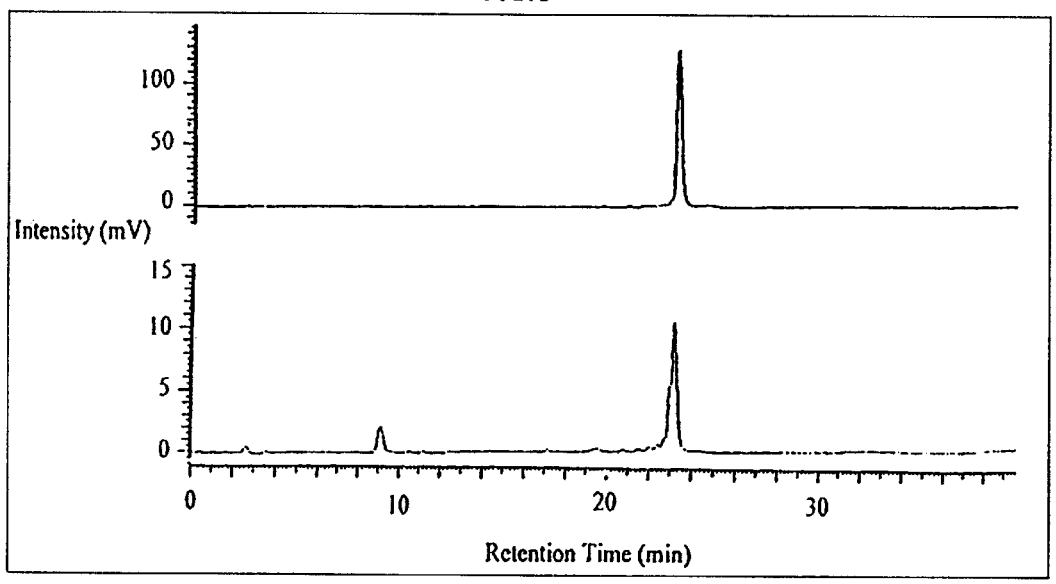
FIG. 5: Example of the qualities of oligonucleotide synthesis products prepared in a conventional synthesiser on conventional support resin (top) and on PE frit material derivatised according to FIG. 4, Type 1

Sequence: decameric thymidylate ("Tr-off"), fully deprotected;
Automated apparatus: Pharmacia Gene Assembler;
Support material: Pharmacia T support (CPG);
Linker: succine
Synthesis: optimised
Sequence: decameric thymidylate ("Tr-off"), fully deprotected;
Automated apparatus: Pharmacia Gene Assembler;
Support material: functionalised PE frits (IRIS 45);
Linker: succinate;
Synthesis: not optimised

REFERENCE (2) Ronald Frank, Simultane kombinatorische Synthese: Moleküle nach MaB durch Screening aus der Vielfalt. In: GBF, Gesellschaft für Biotechnologische Forschung mbH, Braunschweig, wissenschaftlicher Ergebnisbericht (1993), 5–16
(5B) Frank & Doring in Tetrahedron, 44 (1988), 6031–6040
(5C) Frank et al. in Nucleic Acids Res. 11 (1983), 4365–4377
(6) Bray et al. in Tetrahedron Letters, 40 (1990), 5811–5814
(7) Hoffmann & Frank in Tetrahedron Letters, 42 (1994), 7763–7766
(8) DE P 43 20 260.8; DE 44 31 317.9; PCT/EP 94/01896
(9A) EP 85 110 454.7=0 174 525
(14) Jung & Beck-Sickinger in Angew. Chem., 104 (1992), 375–500
(15) Frank in Bioorg. Med. Chem. Letters, 3 (1993), 425–430
(16) Lashkari et al. in PNAS, 92 (1995), 7912–7915
(17A) Moraj et al. in Biochem. J. 316 (1996), 193–199
(17B) Deibel et al. in Peptide Res., 2 (1989), 189–194
Our ref.: 9199
New International Patent Application on the basis of DE (1)97 06 089.7
1. Gesellschaft fuer Biotechnologische Forschung mbH
2. ABIMED Analysen-Technik GmbH
3. IMB Institut fuer Molekulare Biotechnologie e.v. Frank et al; apparatus for automated chemical synthesis

Figure 8:
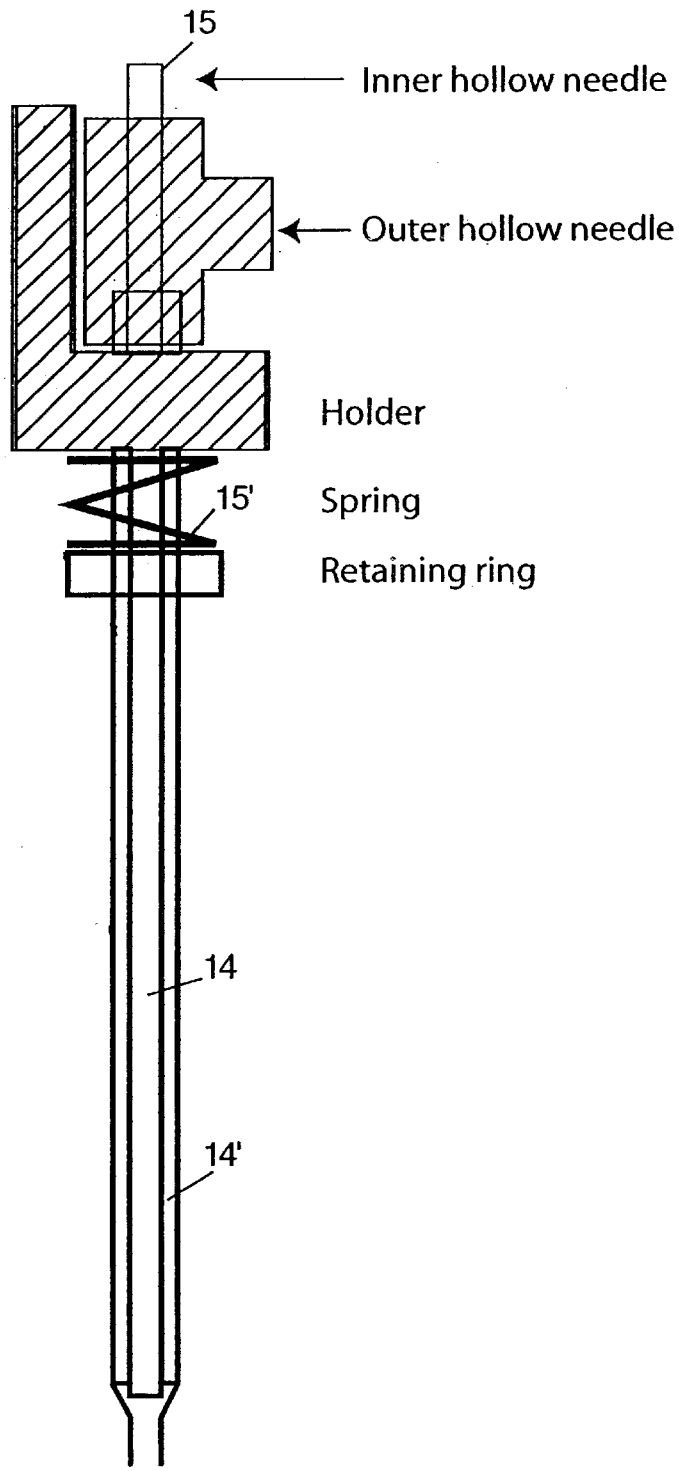
FIG. 8: Diagram of the double hollow needle with a spring loading.

What is claimed is:

1. An apparatus for an automated simultaneous chemical synthesis and optional purification which apparatus has separate reaction vessels/reactors (4), which are open at the top and at the bottom, in the form of channels/reaction channels or columns/reaction columns which are arranged in parallel in a block/reactor block (9) and which are removable either together or separately; wherein a solid phase support material (5) for the synthesis is placed in the reaction vessels/reactors (4), said support material either being arranged between two inert porous frit plates (6, 6') or being itself in the form of chemically modified frit or filter plates, so that liquid media added from above can be held in the reaction vessels/reactors (4) solely as a result of surface tension and wetting of the support material (5); and optionally an inert gas supply is provided, and the block/reactor block (9) is mounted on a trough (7) connected to a vacuum pump (11) by means of a switchable valve (18) so that liquid media can be aspirated simultaneously from the reaction vessel/reactors (4) and the support materials (5) contained therein, wherein the upper inlets to the reaction vessels/reactors (4) in the reactor block (9) are covered by a perforated screen (10) mounted above them or a baffle plate (10) mounted above them, so that the reaction vessels/reactors (4) can be flooded with an inert gas and the flow of inert gas can optionally be increased considerably during the aspirating procedure; or the space above the reaction vessels/reactors (4) can be selectively closed off by means of a displaceable perforated screen so that the reagents can be blown out of the reaction vessels/reactors (4) by pressurized inert gas;

wherein the apparatus is provided with an xyz-pipetting robot, having electronically controllable dispensing syringes/dilutors (15, 15', 15") having one or more dispensing needles (13) and optionally, in addition, having one or more dispensing manifolds (19), so that chemical building blocks, reagents and solvents can be distributed to the reaction vessels/reactors (4) and each of the reaction vessels/reactors (4) can be addressed individually; and wherein each dispensing needle (13) is equipped with a plurality of, at least two, internal channels, which are connected to separate dispensing syringes/dilutors (15, 15', 15") wherein the internal channels can be filled separately by the separate dispensing syringes, and wherein the ends of which channels meet only shortly before the outlet (FIG. 8), so that, when a plurality of reagents are being dispensed simultaneously, mixing occurs only shortly before delivery of the tip of the dispensing needle (13); a channel optionally being connected to the inert gas supply also, so that a pulse of inert gas can expel the mixed volume.

2. The apparatus according to claim 1, wherein the dispensing needles (13) are mounted so as to be resilient along the longitudinal axis, so that they can be set down on the support material (5) or top frits (6) in the reaction vessels/reactors (4), and so volumes down to 1 nanoliter can be reliably deposited.

3. The apparatus according to claim 1, wherein sealed vessels (22) are provided which are sealed by means of septa and provided in a reagent block (21) separate from the reactor block (9) for a number of chemical building blocks (3) and reagents (2).

4. The apparatus according to claim 3, wherein the necks of the sealed vessels (22) in the reagent block (21) are sealed by means of septa and covered by a perforated screen, mounted above them, so that they can be flooded with inert gas.

5. The apparatus according to claim 1, wherein transfer ports (16), which are connected to storage vessels/storage bottles (17, 17', 17", 17''', 17$^{iv}$) either directly or by means of switchable valves (18) (FIG. 6), those storage vessels/storage bottles (17, 17', 17", 17''', 17$^{iv}$) optionally being arranged to be slightly pressurized, so that reagents can also be withdrawn from transfer ports (16) by means of dispensing needles (13).

6. The apparatus according to claim 1, wherein solvent bottles (12) dispensing syringes (15, 15', 15") and one or more dispensing manifolds (19) are provided, so that a component selected from solvents and reagents can be distributed from solvent bottles (12) by means of dispensing syringes (15, 15', 15") or by pressurized inert gas and also by way of one or more dispensing manifolds (19) simultaneously to a plurality of reaction vessels/reactors (4), row by row.

7. The apparatus according to claim 1, wherein the support material (5) forms a layer in the channel of the reaction vessel/reactor (4), through which an even flow of a component selected from applied reagents and solvents can pass solely under the action of gravity.

8. The apparatus according to claim 1, wherein a control computer is provided which uses a list of ASCII words of software wherein the chemical building blocks/monomers used for building up the products are coded as ASCII characters and the products are therefore described as a sequence of build-up reactions/monomer incorporation reactions by means of ASCII words, for the totality of all products for a synthesis program to be converted into valve-switching operations, dispensing-syringe movement operations and robot arm movement operations, wherein each monomer incorporation comprises of a succession of several reaction steps and switching operations.

9. The apparatus according to claim 1, wherein an arrangement of affinity columns is provided which is complementary to the arrangement of reaction vessels/reactors (4).

10. The apparatus according to claim 1, wherein the apparatus has from 10 to 1,000 separate reaction vessels/reactors (4).

11. The apparatus according to claim 10, wherein the apparatus has 48 or a multiple thereof of separate reaction vessels/reactors (4).

12. The apparatus according to claim 11, wherein the apparatus has 400 separate reaction vessels/reactors (4).

13. The apparatus according to claim 1, wherein the separate reaction vessels/reactors (4) are small columns.

14. The apparatus according to claim 1, wherein the vessels (22) are provided in a reagent block (21) for 2 to 100 chemical building blocks (3) and reagents (2).

15. The apparatus according to claim 14, wherein vessels (22) are provided in a reaction block (21) for 24 chemical building blocks (3) and reagents (2).

16. The apparatus according to claim 14, wherein the necks of the vessels (22) are covered by a baffle plate.

17. The apparatus according to claim 1, wherein an arrangement of collection vessels (20) is provided which is complementary to the arrangement of reaction vessels/reactors (4).

18. The apparatus according to claim 1, wherein an arrangement of a affinity columns is provided which is complementary to the arrangement of reaction vessels/reactors (4) and an arrangement of collection vessels (20) is provided which is also complementary to the arrangement of reaction vessels/reactors (4).

* * * * *